(12) United States Patent
Gruden

(10) Patent No.: US 9,347,906 B2
(45) Date of Patent: May 24, 2016

(54) SENSOR APPARATUS FOR DETECTING PROPERTIES OF LIQUID

(71) Applicant: Seuffer GmbH & Co. KG, Calw (DE)

(72) Inventor: Roman Gruden, Pforzheim (DE)

(73) Assignee: Seuffer GmbH & Co. KG, Calw (DE)

( * ) Notice: Subject to any disclaimer, the term of this patent is extended or adjusted under 35 U.S.C. 154(b) by 434 days.

(21) Appl. No.: 13/742,443

(22) Filed: Jan. 16, 2013

(65) Prior Publication Data
US 2013/0214797 A1      Aug. 22, 2013

(30) Foreign Application Priority Data

Jan. 20, 2012   (DE) ............... 20 2012 000 569 U

(51) Int. Cl.
| | |
|---|---|
| *G01R 27/26* | (2006.01) |
| *G01N 27/22* | (2006.01) |
| *D06F 39/00* | (2006.01) |
| *G01R 1/00* | (2006.01) |
| *G01N 1/00* | (2006.01) |
| *G01N 33/18* | (2006.01) |
| *A47L 15/42* | (2006.01) |
| *G01N 27/30* | (2006.01) |

(52) U.S. Cl.
CPC ............ *G01N 27/221* (2013.01); *D06F 39/004* (2013.01); *A47L 15/4297* (2013.01); *G01N 1/00* (2013.01); *G01N 27/30* (2013.01); *G01N 33/18* (2013.01); *G01N 2201/00* (2013.01); *G01R 1/00* (2013.01)

(58) Field of Classification Search
CPC ....... G01N 1/00; G01N 2201/00; G01R 1/00; G01F 1/00; G01F 11/00; G01F 17/00; G01F 23/00
USPC ............. 324/437–439, 445, 446, 448–450, 324/750.08, 750.17, 754.04, 754.07, 324/754.16, 756.07, 553, 609, 663, 664, 324/667, 668, 674, 675, 689, 692–694, 698
See application file for complete search history.

(56) References Cited

U.S. PATENT DOCUMENTS

| | | | | | |
|---|---|---|---|---|---|
| 3,010,320 | A | * | 11/1961 | Sollecito ............. | 73/304 C |
| 4,820,973 | A | * | 4/1989 | Alvarez ............... | 73/304 C |

(Continued)

FOREIGN PATENT DOCUMENTS

| | | |
|---|---|---|
| DE | 217557 A1 | 1/1985 |
| DE | 38 12 687 A1 | 10/1989 |

(Continued)

OTHER PUBLICATIONS

Dietmar Ende, et al; "Impedanzspektroskopie"; Chemie in Unserer Zeit, Bd. 27, Nr. 3, Jul. 1993; pp. 134-140.

*Primary Examiner* — Huy Q Phan
*Assistant Examiner* — Temilade Rhodes-Vivour
(74) *Attorney, Agent, or Firm* — Ware, Fressola, Maguire & Barber, LLP

(57) ABSTRACT

The invention relates to a sensor device for detecting properties of fluid media in a container, comprising at least one base plate (42) made of an insulating material and having a first surface (42*a*) exposed to the medium (3), at least two sensor elements (41) having at least a first and a second electrode (41*a*, 41*b*) arranged insulated from one another on the first surface of the base plate and around which the medium flows, the at least two sensor elements being arranged in a predetermined spatial position relative to each other.

8 Claims, 12 Drawing Sheets

(56) References Cited

U.S. PATENT DOCUMENTS

| | | | | |
|---|---|---|---|---|
| 5,017,879 A | * | 5/1991 | Lucas | G01N 27/226 324/663 |
| 5,151,660 A | * | 9/1992 | Powers | G01L 9/0005 324/663 |
| 5,973,503 A | * | 10/1999 | Kuipers et al. | 324/698 |
| 7,143,637 B1 | | 12/2006 | McBrearty et al. | |
| 7,834,646 B2 | * | 11/2010 | Chambon et al. | 324/698 |
| 2004/0085080 A1 | * | 5/2004 | Schilowitz et al. | 324/698 |
| 2005/0247114 A1 | | 11/2005 | Kahn et al. | |
| 2006/0105467 A1 | * | 5/2006 | Niksa et al. | 436/150 |
| 2007/0112398 A1 | * | 5/2007 | Stevenson et al. | 607/63 |
| 2009/0119041 A1 | * | 5/2009 | Hu | G01N 27/026 702/65 |

FOREIGN PATENT DOCUMENTS

| | | |
|---|---|---|
| DE | 195 11 556 C1 | 7/1996 |
| DE | 19611174 C1 | 7/1997 |
| DE | 19755418 A1 | 6/1999 |
| DE | 100 42 846 A1 | 5/2002 |
| DE | 102 12 494 A1 | 10/2003 |
| DE | 11 2005 000168 T5 | 11/2006 |
| WO | 00/63682 A2 | 10/2000 |
| WO | 03/104798 A1 | 12/2003 |
| WO | 2011/064770 A2 | 6/2011 |

* cited by examiner

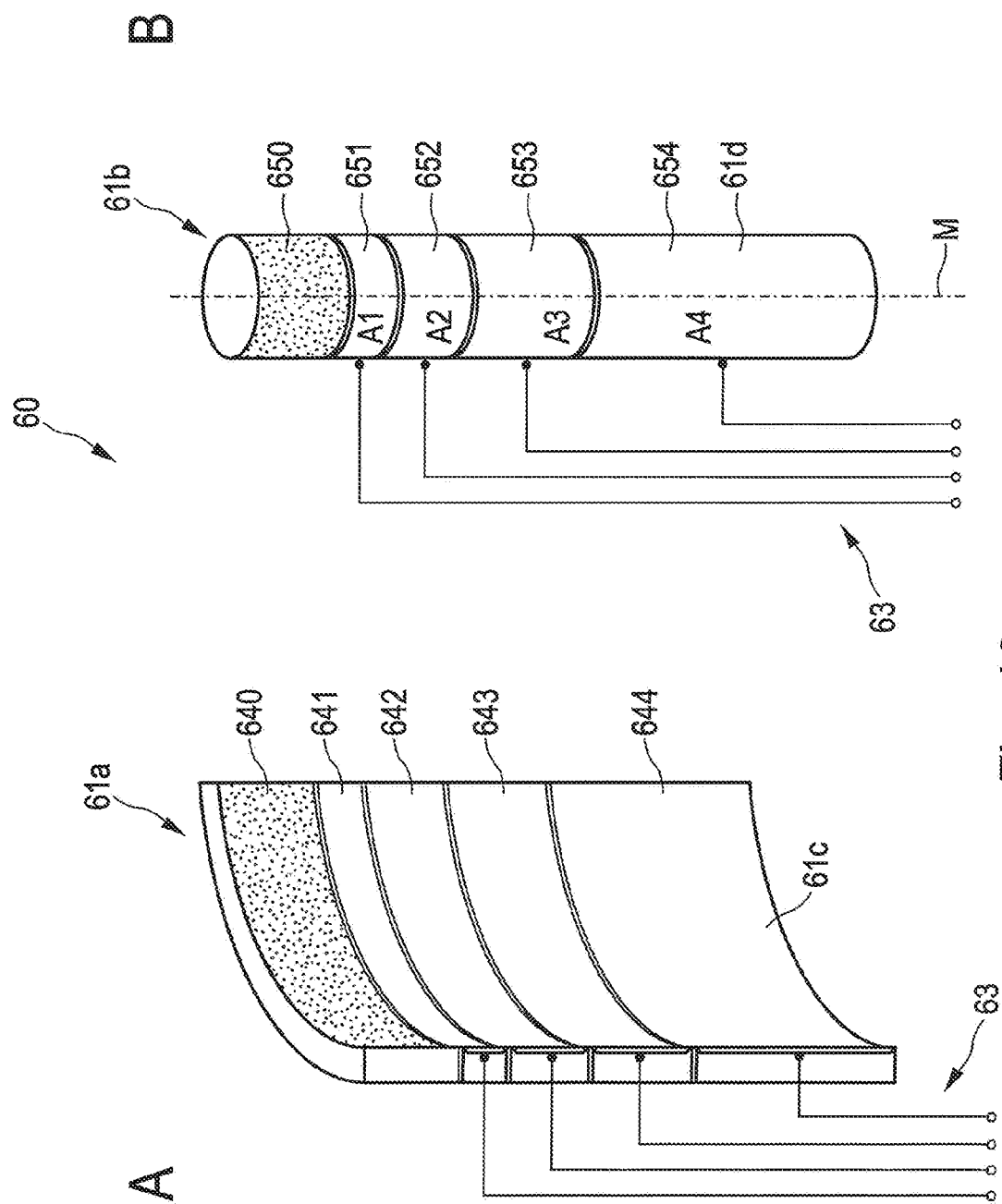

SENSOR APPARATUS FOR DETECTING PROPERTIES OF LIQUID

CROSS REFERENCE TO RELATED APPLICATIONS

This application claims priority under 35 USC §119 to German Patent Application No. 202012000569.3 filed on Jan. 20, 2012, which application is hereby incorporated by reference in its entirety.

TECHNICAL FIELD

The present invention relates to a sensor device for detecting properties of liquids, and in particular to an apparatus for detecting properties of aqueous solutions.

BACKGROUND OF THE INVENTION

An electrodeless sensor for measuring the conductivity of aqueous solutions is known from the prior art in document DE 196 11 174 C1, where three transformers are used. A first transformer is connected to a liquid being measured and transforms a generator AC voltage into a magnetic field, and the liquid being measured is penetrated by the magnetic field which is produced by the first transformer from the generator AC voltage. A second and a third transformer are also provided, which are both coupled to the first transformer via the magnetic field that is present in the liquid. Each of the two additional transformers, which function as output transformers, is tuned to a different resonance frequency such that the two resonance frequencies are offset from each other. Addition of the two output voltages results in a wideband frequency response under the material influence of the liquid being measured. The output signals of the two additional transformers are analyzed to determine the conductivity of the liquid being measured, which is in the form of an aqueous solution, with any coupled interference signals being cancelled by appropriate circuitry.

Document DD 217 557 A1 discloses a method for controlling the addition of detergents or dish soap in washing machines, with various sensors being arranged in a washing machine in order to determine the physical and chemical properties of the detergent solution. Any change in the rise of the measurement signal during the addition of detergent or dish soap is detected and analyzed by an electronic circuit for analyzing the output signals of the sensors. The dosing of detergent for the washing machine can be controlled on that basis.

Document DE 197 55 418 A1, finally, discloses a sensor element and an apparatus for measuring complex impedances in materials, said sensor element comprising two electrodes made of a conductive material and arranged at a predetermined distance from each other. The two electrodes are covered with a thin insulating layer having a relatively small thickness in comparison to the predetermined gaps. The sensor element thus formed is largely insensitive to the surrounding media whose properties are to be detected. The output signals from the sensors are subjected to further processing in an evaluation circuit, and the properties of a respective liquid between the electrodes can be analyzed. More specifically, it is possible for complex impedances to be determined and analyzed as a measure of the liquid's properties.

Corresponding to the aforementioned known ways of detecting the properties of a detergent solution, for example, or of other fluid media, parameters for the properties of the media being studied can be specified with the devices described and by relatively complicated analysis of the measurement results. In particular, there is generally a strong need to detect material properties such as the quality of oil in an internal combustion engine, in order to change the oil when the properties of the oil being used deteriorates. A brake fluid in motor vehicles or a general hydraulic oil can likewise be checked for properties that can vary in operation.

The known ways, described in the foregoing, of detecting the properties of liquids such as a detergent solution or other aqueous solutions are devices and systems by means of which, in combination with a relatively complicated analysis of the measurement results and complex sensor units, the properties or at least individual parameters of the respective fluid being examined are determined.

Efforts to make a washing process both ecofriendly and optimized produce a strong need to detect the properties of a detergent solution in a washing device at the beginning of and throughout the washing process, so that the amount of water and/or the amount of detergent being used, for example, is precisely determined to create less pollution, and so that the amount of detergent for washing the laundry can be precisely dosed according to the level of contamination, or depending on particular properties of the water (mineral content, water hardness).

Systematic and correct dosing of detergent results in energy and water savings, as well as the desired reduction of wastewater pollution. A detection means for detecting detergent solution in a washing device, in respect of the detergent concentration or level of contamination, for example, should be of simple construction and operationally reliable. Since the aim is for more and more washing devices in private households and in industry to be equipped with a detection means for detecting the properties of the detergent solution, there is a strong need for sensor devices of simple construction that can be manufactured in large numbers at low cost and which can nevertheless provide reliable detection results for further analysis. Every washing device should ideally be equipped with such a detection means or sensor device, so that requirements for uncomplicated assembly during production of the washing device can also be taken into consideration, in addition to the requirement for simple construction.

SUMMARY OF THE INVENTION

The object of the present invention is therefore to design a sensor device, for detecting properties of liquids, in such a way that simplicity of construction and concomitantly low-cost production are combined with reliable detection of the properties of a fluid.

According to the invention, this object is achieved by the features specified in the claims.

According to a first aspect of the invention, the inventive sensor device for detecting properties of fluid media in a container comprises at least one base plate made of an insulating material and having a first surface exposed to the medium, at least two sensor elements having at least one first and one second electrode arranged insulated from one another on the first surface of the base plate and around which the medium flows, the at least two sensor elements being arranged in a predetermined spatial position relative to each other.

Alternatively, according to a second aspect of the invention, the inventive sensor device for detecting properties of fluid media in a container comprises a base plate made of an insulating material and having at least one first surface exposed to the medium, at least one sensor element embodied as a cylindrical capacitor and comprising at least one outer electrode and one inner electrode partially surrounded by said outer electrode, wherein the at least one outer and the inner electrode extend from the first surface of the base plate, and wherein the at least one outer electrode and the inner electrode are subdivided in the direction of extension into a plurality of electrode sections insulated from one other, and the outer, and the inner electrode are subdivided in the same manner.

The present invention thus relates to a sensor device for detecting material properties, and in the present case for detecting properties of a fluid, such as a detergent solution or other aqueous solutions, the sensor device being substantially designed as a capacitive sensor according to the details specified in the claims. Such electrodes are arranged spaced apart and insulated from each other on one side of an insulating base plate.

It is possible with the arrangement of the sensor device according to the invention to detect various properties of a medium of interest in a reliable manner, for example of a detergent solution or other aqueous solutions, the sensor device simultaneously being of simple construction. This simple construction allows the sensor device to be manufactured cost-efficiently. This is particularly advantageous when producing the sensor device in larger quantities for a series of washing devices or other applications.

The sensor device allows the properties of aqueous solutions to be detected with precision, and as a consequence of its cost-efficient production, also in larger quantities, can also be deployed in washing devices for private households or industry, for example. It is likewise possible by means of the sensor device according to the invention to detect any change in the properties of the fluid medium of interest, for example of fresh water (mineral content, water hardness) or also of wastewater (changing level of contamination). Different embodiments are suitable for different applications or fields of application. With these sensor devices, it is possible to detect a plurality of properties (parameters of interest) of the fluid medium, either simultaneously or in a predefined sequential manner. However, all embodiments are based on a construction that can be manufactured and deployed cost-efficiently while still providing reliable detection.

Further embodiments of the invention are specified in the dependent claims.

According to the first aspect of the invention, a plurality of similar sensor elements may be arranged on the first surface, wherein each sensor element can be driven via individual connection lines.

The plurality of sensor elements may be configured identically or differently, wherein the dimensions of the differently configured sensor elements may be in predetermined gradations.

At least two base plates arranged parallel and opposite each other may be provided, at least one sensor element being arranged on the first opposite sides of each base plate, and each sensor element and each electrode of the sensor element can be individually driven.

The at least one sensor element of the first base plate may be mirror-symmetrical to the at least one sensor element of the second base plate.

The at least one sensor element arranged on one of the base plates may have an outer electrode and an inner electrode partially surrounded by said outer electrode, or may have a pair of electrodes embodied as an interdigitated structure.

According to the second aspect of the invention, the electrode sections of the outer and inner electrodes are each connected to connection lines and can be selected individually and independently of each other.

The at least one outer and the inner electrode may be subdivided into a plurality of identical or different electrode sections, and the electrode sections formed by non-identical subdivision may be subdivided, in respect of their extension in the direction of extension, in predetermined ratios to each other.

The individual sensor elements may be made of the same conductive material or of different conductive materials.

The individual electrode sections may also be made of the conductive material or of different conductive materials, wherein respectively matching electrode sections of the outer and inner electrodes may be made of the same material.

BRIEF DESCRIPTION OF THE DRAWINGS

The invention shall now be described on the basis of embodiments and with reference to the Figures, in which:

FIG. 12 shows a schematic view of parts of the sensor device shown in FIG. 10, according to a second variant.

DESCRIPTION OF PREFERRED EMBODIMENTS

Figure 1:
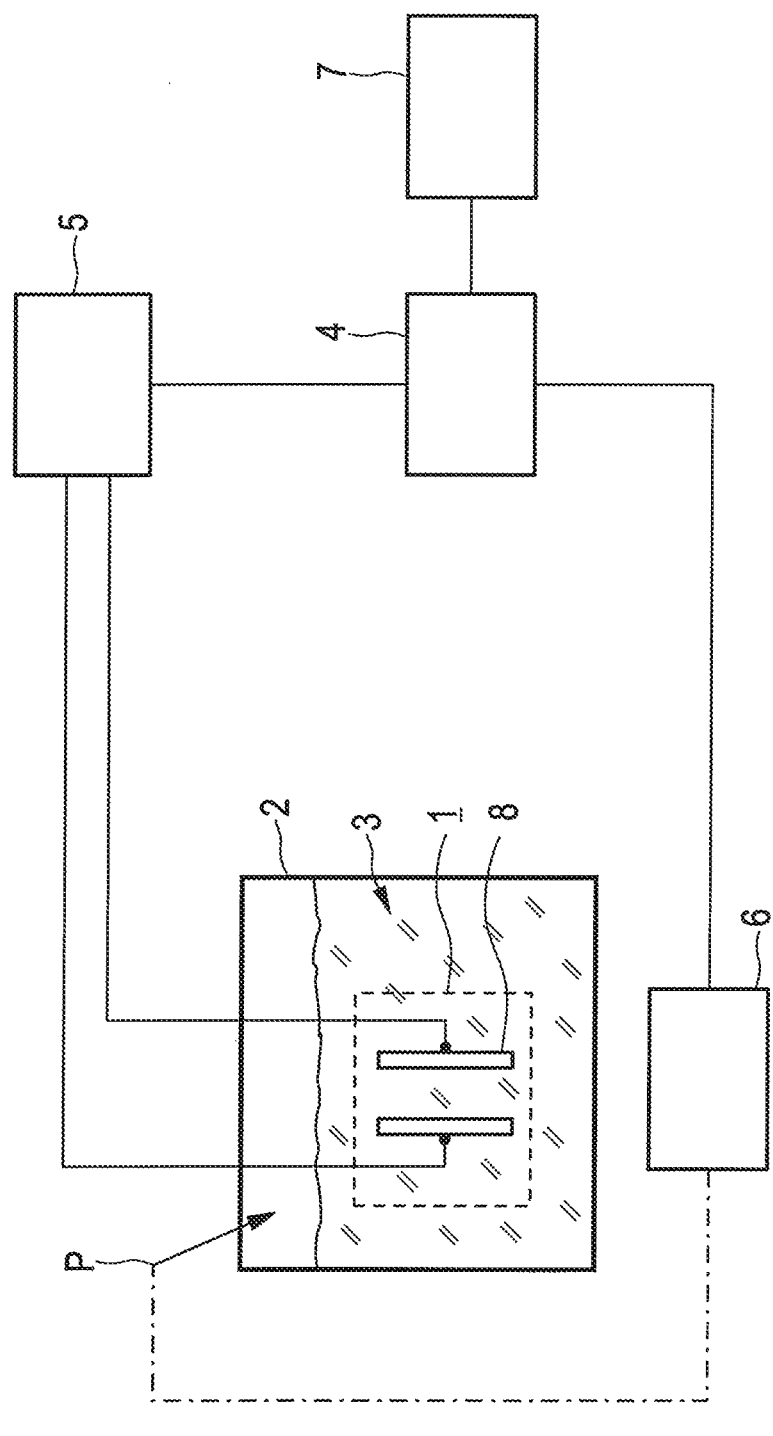
FIG. 1 shows a block diagram of a circuit arrangement for performing measurements in conjunction with the sensor device according to the invention.
Figure 2:
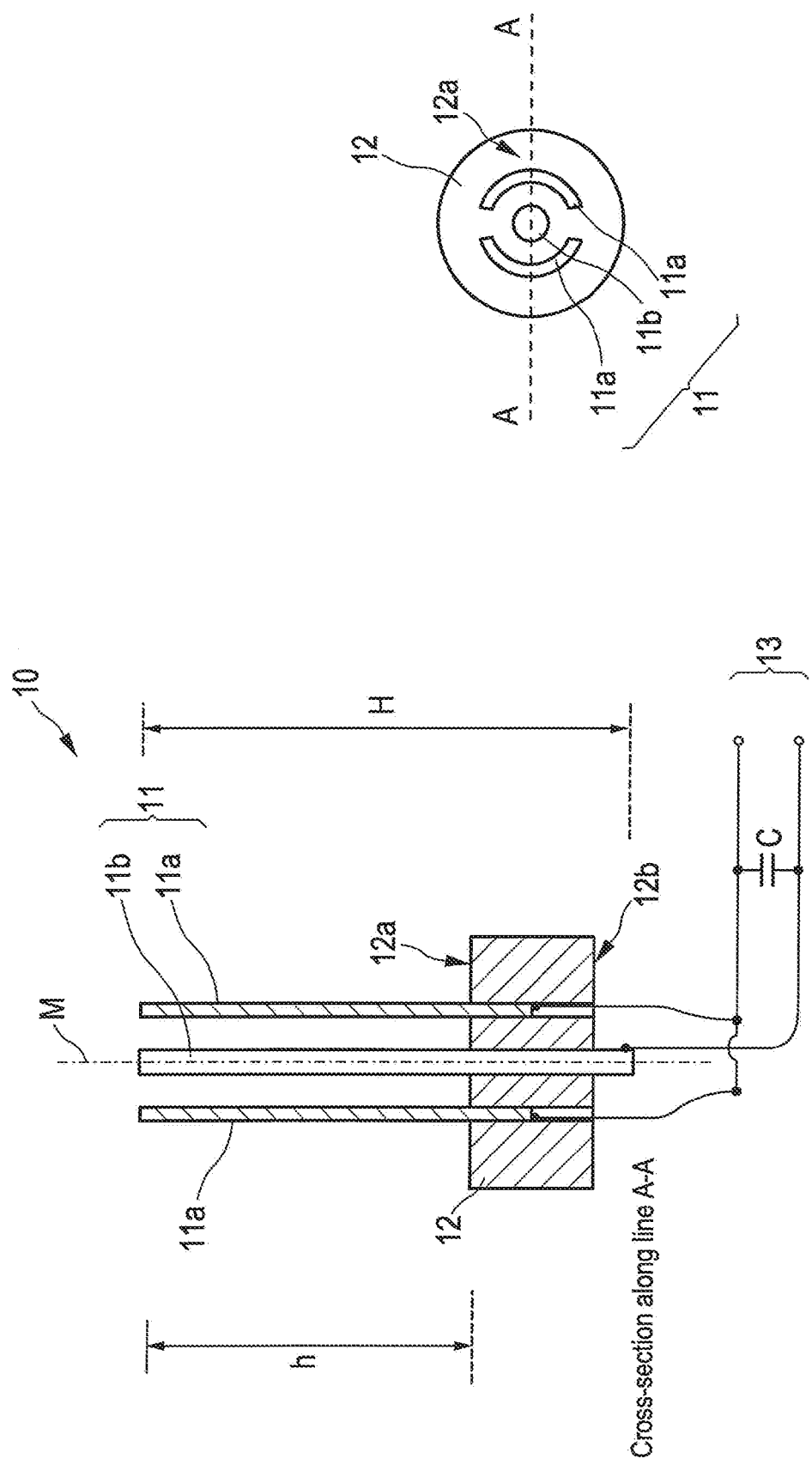
FIG. 2 shows a perspective view of the sensor device according to FIG. 1.
Figure 3:
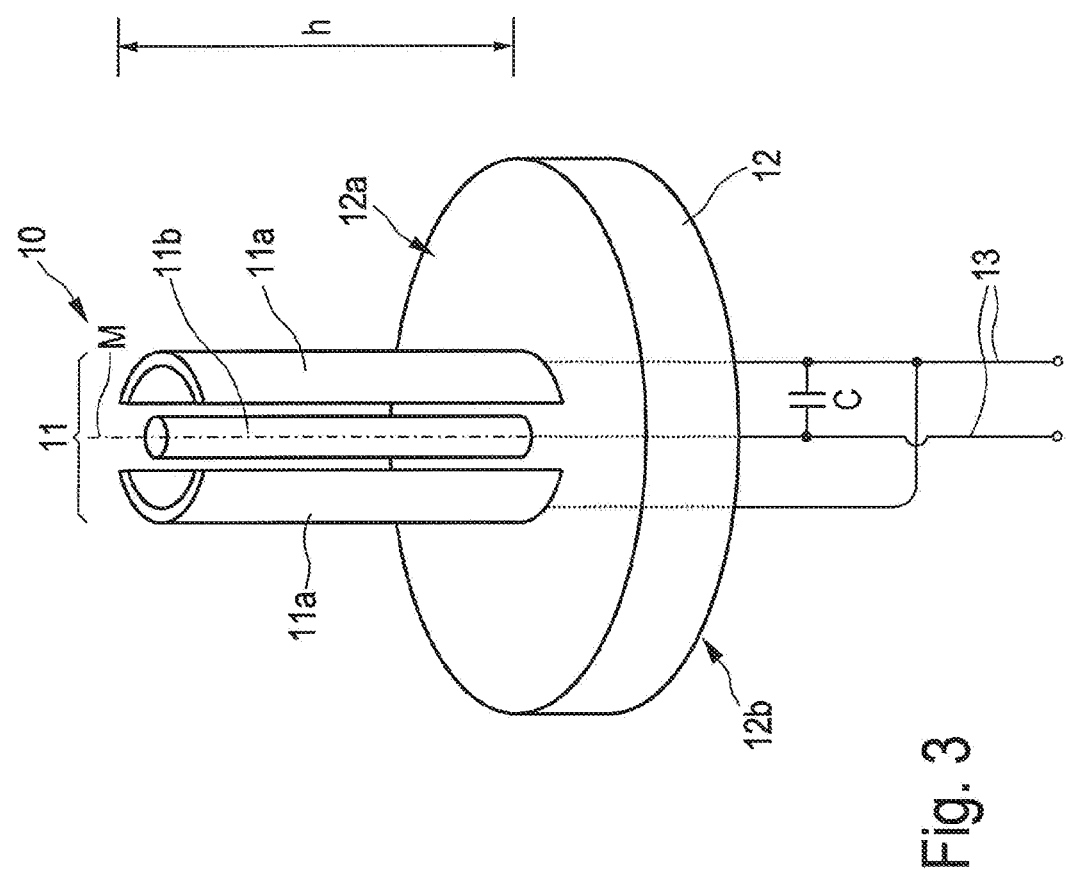
FIG. 3 shows a schematic view of the sensor device in FIG. 1, according to a first embodiment.
Figure 4:
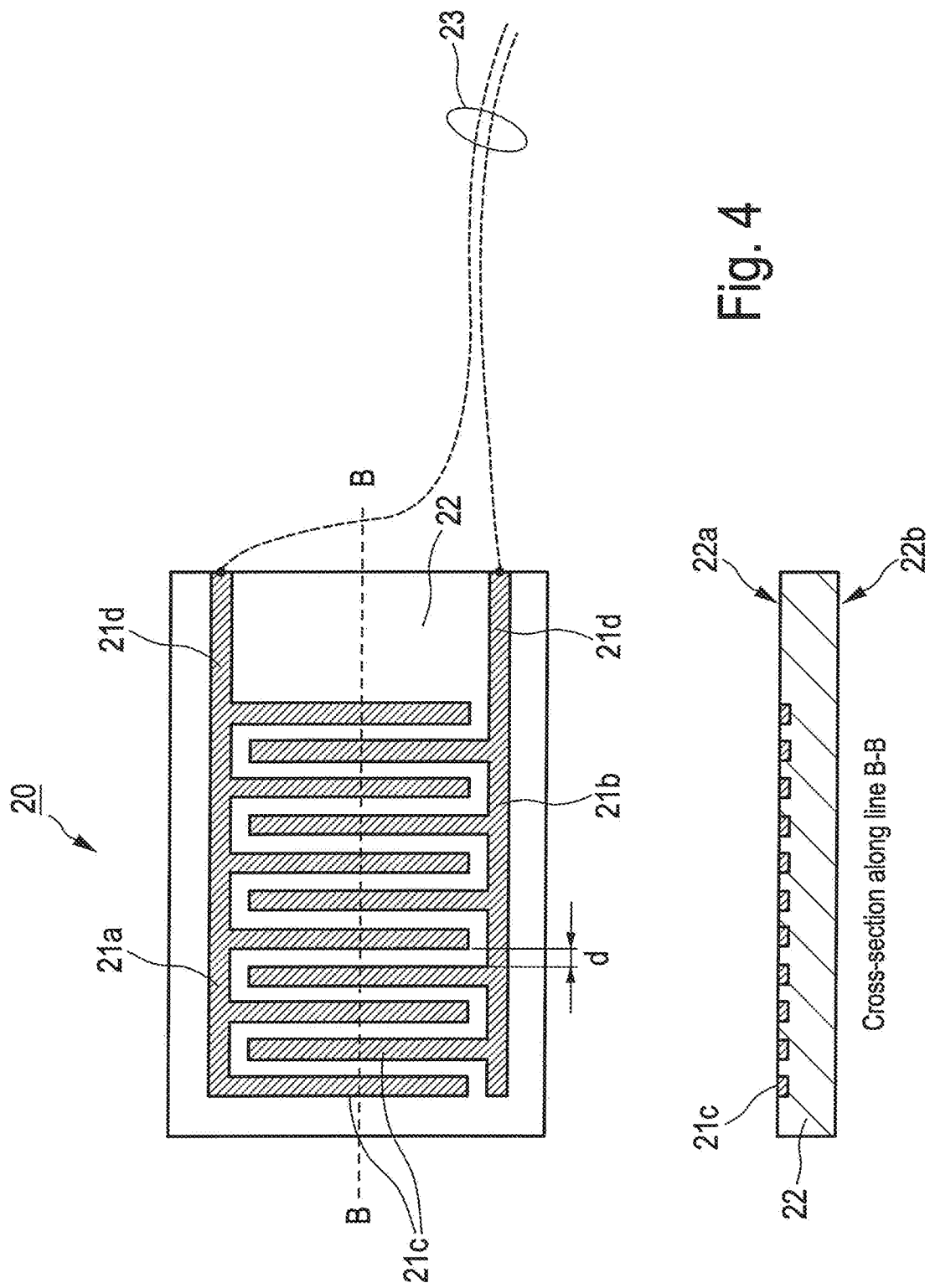
FIG. 4 shows a schematic view of the sensor device in FIG. 1, according to a second embodiment.

The basic construction, manner of operation and the selection of a sensor device 1 according to the present invention shall now be described with reference to the schematic block diagram shown in FIG. 1. Sensor device 1 is shown in FIG. 1 in a purely schematic, simplified form, namely as a capacitive sensor comprising two symbolic capacitors, whereas FIGS. 2-4 show specific variants of sensor device 1. These variants are described further below.

To illustrate the use of sensor device 1 for detecting properties of a liquid medium, for example of an aqueous solution, FIG. 1 shows a schematic block diagram containing various components that are suitable for performing measurements and by means of which sensor device 1 is driven.

According to FIG. 1, sensor device 1 is arranged in a container 2 containing a fluid medium 3. The expression "container" 2 should be understood in a general sense, and the container may be a tank in an apparatus or machine, or the drum of a washing device (washing machine), or the like. In any case, container 2 contains the medium 3 whose properties are to be detected and which is preferably an aqueous solution in an amount sufficient for the properties of medium 3 to be detected by means of sensor device 1. At the least, it is possible to measure a parameter of interest by means of sensor unit 1 and by controlling it accordingly. Detection may be continuous or may be carried out at predetermined intervals or whenever required. Control by means of computer software is a possible option.

In order to perform a reliable measurement, sensor device 1 is surrounded wholly or at least partially by medium 3. In the following description, sensor device 1 is arranged by way of example in a detergent solution (medium 3) of a washing device (washing machine). By means of sensor device 1, the detergent solution is checked for the concentration of a detergent, for example, or for a level of contamination. The invention is not limited to the latter parameters, however. Rather, it is possible to measure other parameters of the aqueous solution being analyzed. For example, the properties of fresh water (such as concentration of contaminants, or water hardness) may be determined, or a washing process may be controlled or regulated according to the detected properties of a fresh water sample.

In order to perform the respective measurement, sensor device 1 is connected to a control unit 4, for example, which is used to control the entire procedure for detecting the properties of medium 3 and which also causes sensor device 1 to be driven, and performs an analysis of the signals (detection signals) outputted by sensor device 1. For this purpose, control unit 4 is connected to a drive unit 5, which drives sensor device 1 with the respective electrical signals according to instructions and commands from control unit 4. For example, electrical voltages are applied in combination with predetermined frequencies or frequency ranges to sensor device 1 (i.e., to the sensor devices in the embodiments described in the following) in order to perform the respective measurements. A method may be used here in combination with impedance spectroscopy.

Control unit 4 is also provided for detecting the temperature of medium 3 and for that purpose may be connected to a temperature detection device which is disposed in container 2 but not shown in the Figures. The functions of sensor device 1 and drive unit 5 may also be consolidated in a single device, which may then be referred to as a measuring device, for example. Control unit 4 is also connected to a main control unit 6, which is directly associated, for example, with the washing device in which container 2 is disposed. If container 2 is the container for the detergent solution, and includes the drum of the washing device, main control unit 6 is the actual electronic control unit for the washing device.

The volume of water, the supply of detergent and operation of the motor are controlled in the washing device in the respective and programmed manner. Depending on the measurement results obtained from operation of sensor device 1, control unit 4 may influence the main control unit 6 such that a larger or smaller amount of water, or a larger or smaller amount of detergent can be used, or that a change can be made in the washing temperature, according to the information obtained, and in deviation from a predetermined program, for example. Control unit 4, in combination with main control unit 6, permits variable control of the washing device, or regulation of the entire washing device system. The general influence exerted by main control unit 6 on the washing process is shown symbolically in FIG. 1 by a broken lines and an arrow P in the direction of container 2.

Control unit 4 may also be in communication with a storage device 7, in which the respective data and programs for performing the respective measurements, i.e., for detecting the material properties of medium 3, can be stored, and to which control unit 4 can have access when necessary, and in which captured or processed data may also be stored.

When performing measurements using sensor device 1, it is possible, according to the above description of sensor device 1, for predefined variables such as current and voltage, in combination with respective frequencies, to be supplied by drive unit 5 in response to respective instructions from control unit 4. In connection with the measurement being performed, the detection signals from sensor device 1 are recorded and processed by control unit 4 via drive unit 5, if necessary in combination with programs or data fetched from storage device 7. For example, a comparison can be made with basic data on the properties of medium 3 being analyzed, in order to detect any absolute or relative changes, although it is also possible for any changes occurring to be detected during predefined processes of extended duration.

Depending on the detection result, for example according to the detected concentration of the detergent solution being analyzed in the washing device, main control unit 6 may be instructed to change or maintain particular operating parameters, and the measurement results may be stored in storage device 7 for subsequent tracking of measurement results and processes in the washing device.

Whereas the arrangement of sensor device 1 within a measuring system or a control and regulation system is specified in FIG. 1, as described in the foregoing. FIGS. 2-4 show respective embodiments of sensor device 1 that are used instead of the sensor device 1 according to FIG. 1 and which can be operated accordingly.

First Embodiment

FIGS. 2 and 3 show a first embodiment of sensor device 10. FIG. 2 shows a plan view of the layout of sensor device 10, as well as a cross-section along line A-A. FIG. 3 shows a perspective view of sensor device 10.

In the view according to FIG. 1, the symbolically represented sensor device 1 is simplified as a capacitive sensor and schematically represented by two capacitor plates 8 arranged one opposite the other. The schematic capacitor plates illustrate the basic principle of a parallel plate capacitor, between the plates of which there is a material having dielectric properties that are predefined and/or to be detected. In the present case, as shown in FIG. 1, and in combination with observations concerning a washing device, the dielectric material is formed by medium 3, and for example by an aqueous solution such as a detergent solution.

According to the view in FIGS. 2 and 3, the sensor device 10 of the first embodiment includes a sensor arrangement in which electrodes (instead of the schematic capacitor 8 according to FIG. 1) in the form of individual electrodes 11 are arranged opposite each other. More specifically, electrodes 11 of the sensor device 10 are arranged, according to the first embodiment, in such a way that at least one outer (first) electrode 11a and, in the specific case of FIGS. 2 and 3, two outer electrodes 11a embodied as part of an outer surface of a hollow cylinder, are arranged opposite an inner (second) electrode 11b disposed substantially at the center of the base area of the hollow cylinder. Each of the outer electrodes 11a is smaller than half of the outer surface of the hollow cylinder, thus forming two separate and spaced apart electrodes in an arrangement similar to that of half shells, between which an interspace is provided in a predetermined manner. Inner electrode 11b runs or extends along the main axis or axis of symmetry of the mentally conceived hollow cylinder created by the two outer electrodes 11a.

All the electrodes 11 are arranged and fixed in a mechanically stable manner in a base plate 12 made of an insulating material, such that a dielectric material and in particular the medium 3 whose properties are to be detected can get between the outer electrodes 11a and the inner electrode 11b, which extend substantially perpendicularly away from base plate 12. Thus, medium 3 flows around the first and the second electrode 11a and 11b.

The two outer electrodes 11a are spaced apart from each other in a predetermined and preferably constant manner, such that an approximately constant gap is formed between one of the outer electrodes 11e and the inner electrode 11b and the respective length of electrodes 11 is approximately the same outside base plate 12. All the electrodes 11 therefore run along the middle axis of the mentally conceived hollow cylinder on one of the side of base plate 12, according to the views shown in FIGS. 2 and 3 on the upper side of base plate 12. The side of base plate 12 on which the electrodes 11 are arranged is referred to as the first side or as the first surface 12a.

On the other side of base plate 12, i.e., on the second side or surface 12b, the respective electrodes 11 are connected to electrical connection lines 13. The at least one outer electrode 11a constitutes the one pole thereby. In the case of the two outer (first) electrodes 11a, these are connected electrically to each other and constitute one and the same pole of the electrode arrangement according to FIGS. 2 and 3. The inner (second) electrode 11b constitutes the other pole and is likewise connected to connection lines 13.

FIG. 2 shows a schematic view of the connection between the respective connection lines 13 and the respective electrodes 11. An optional capacitor C is provided here between the one pole formed by the outer electrodes 11a and the other pole formed by inner electrode 11b. Capacitor C is used to define the frequency range of the drive signals by means of which sensor device 10 is driven. The frequency of particular measurement points in a measuring procedure can be specified with the predetermined capacitance of capacitor C. The respective connection lines 13 are connected to drive unit 5 (FIG. 1) in order to perform respective measurements or to detect properties.

In FIGS. 2 and 3, base plate 12 is shown as an approximately circular disk of predetermined thickness, in the middle of which the inner electrode 11b is disposed, the at least one and preferably two outer electrodes 11a being arranged around said inner electrode 11b at a predetermined distance. The embodiment of base plate 12 as a circular disk is merely an example, and the present invention is not limited to this basic form. Rather, base plate 12 can be of any shape and also of various different thicknesses, and the arrangement of electrodes 11 does not necessarily have to be in the middle of a symmetrically shaped base plate 12. In any case, base plate 12 is inserted into a matching opening in container 2, with appropriate seals between provided in the region of the opening in order to prevent undesired escape of medium 3 from container 2 where sensor device 10 in inserted. Sensor device 10 is preferably located in the lower part of container 2 and it is further preferred that it be located at the lowest point of container 2, so that the properties of medium 3 can be reliably detected even when there only small amounts of medium 3.

The properties of the medium being analyzed pertain, for example, to a concentration of minerals, to detergent substances and to contamination of the detergent solution arising and increasing as a consequence of the washing process. At least one parameter such as a concentration of particular substances can be determined. A temperature sensor unit may be provided additionally on sensor device 10, in particular in the region of base plate 12.

In the view of sensor device 10 shown in FIGS. 2 and 3, a first height h and a second height H are specified. The first height h is the free length of electrodes 11 outside base plate 12 in the region of container 2 being analyzed. Thus, medium 3 flows around this region of the electrodes.

The second height H is the total length of the longest electrode 11, for example of inner electrode 11b, part of the inner electrode 11b being disposed above base plate 12 and another part of it being disposed below base plate 12. The part below base plate 12 thus extends away from the second surface 12b. The connection lines 13 and capacitor C are connected to the part that is below base plate 12.

According to the view shown in FIGS. 2 and 3, the outer electrode 11a comprises two parts that are arranged concentrically, befitting their shape, as part of a hollow cylindrical wall around inner electrode 11b. However, the present invention is not limited to such an arrangement, and it is likewise possible to provide the outer electrodes 11a, arranged concentrically around the inner electrode 11b, in the form of three or more roughly similar parts each extending in a direction perpendicular to a base plate 12 along the middle line M and spaced apart from each other, thus ensuring that medium 3 (fluids) can flow between the individual electrodes even when suspended matter is produced in the course of the washing process. For example, if two pairs of outer electrodes 11a are provided, then two of the four larger electrodes 11a can be insulated from medium 3 in container 2 (i.e., provided with an insulating layer), whereas the two other electrodes are not insulated from the medium. All the parts of the first or outer electrode 11a form one and the same pole.

Alternatively, the at least one first (outer) electrode 11a may also be integrally embodied as a complete hollow cylinder, in the inner space of which the second (inner) electrode 11b runs substantially along an axis of symmetry or middle line (M in FIG. 3). The first electrode 11a, in the form of a hollow cylinder, has some openings in its cylinder wall so that the medium 3 being analyzed can flow around the two electrodes 11 (11a and 11b) and in particular can enter, the space between the electrodes 11. The result, deviating from the plan view in FIG. 2, is then a complete hollow cylinder with respective flow openings ensuring a constant flow of medium around the region between the electrodes 11.

Second Embodiment

FIG. 4 shows a second embodiment of sensor device 20, which is shown in a general form as sensor device 1 in FIG. 1. FIG. 4 shows a plan view onto the layout of sensor device 20, and a cross-section along a line B-B.

According to the second embodiment of the invention, sensor device 20 comprises first and second electrodes 21a and 21b arranged on a shared base plate 22. According to the schematic view shown in FIG. 4, base plate 22 consisting of an insulating material is arranged as a rectangular plate. However, the invention is not limited to such a shape, and base plate 22 may also have any shape deviating therefrom.

The first and second electrodes 21a and 21b are arranged flush on base plate 22 in such a way that said electrodes have single electrode arms 21c extending from one side and arranged alternatingly on base plate 22. The first and second electrodes 21a and 21b engage each other like combs, although all the parts of both electrodes 21a and 21b are spaced apart from each other by a predefined distance d. On base plate 22 made of an insulating material, the two electrodes 21a and 21b are therefore electrically separated from each other and are each electrically associated with a respective pole. The two electrodes 21a and 21b form a capacitive sensor and are arranged on a first side or first surface 22a of base plate 22. An opposite surface is referred to as a second surface 22b.

The two electrodes 21a and 21b have respective terminal regions 21d, to which respective connection lines 23 are connected. Connection lines 23 may be arranged on the first or on the second surface 22a or 22b. In the same manner as in the first embodiment, a capacitor C may be disposed between the first electrode 21a and the second electrode 21b and thus between the two electrical poles.

FIG. 4 also shows a cross-sectional view of sensor device 20 according to the second embodiment along line B-B. It can be seen from this view that the individual parts of the two electrodes 21a and 21b are countersunk and therefore flush with the first surface 22a in the insulating base plate 22. However, the present invention is not limited to such an arrangement, and the electrode portions of the two electrodes 21a and 21b may also be partially countersunk into base plate 22, or may be arranged on top of base plate 22 and in particular on the first surface 22a of same. In any case, all the parts of the first electrodes 21a are spaced apart from the second electrode 21b by a predefined distance d. The region between electrodes 21a and 21b and hence also between electrode arms 22c is in the form of a serpentine on the first surface 22a of base plate 22.

Third Embodiment

A third embodiment of sensor device 30 shall now be described with reference to FIG. 5.

Figure 5:
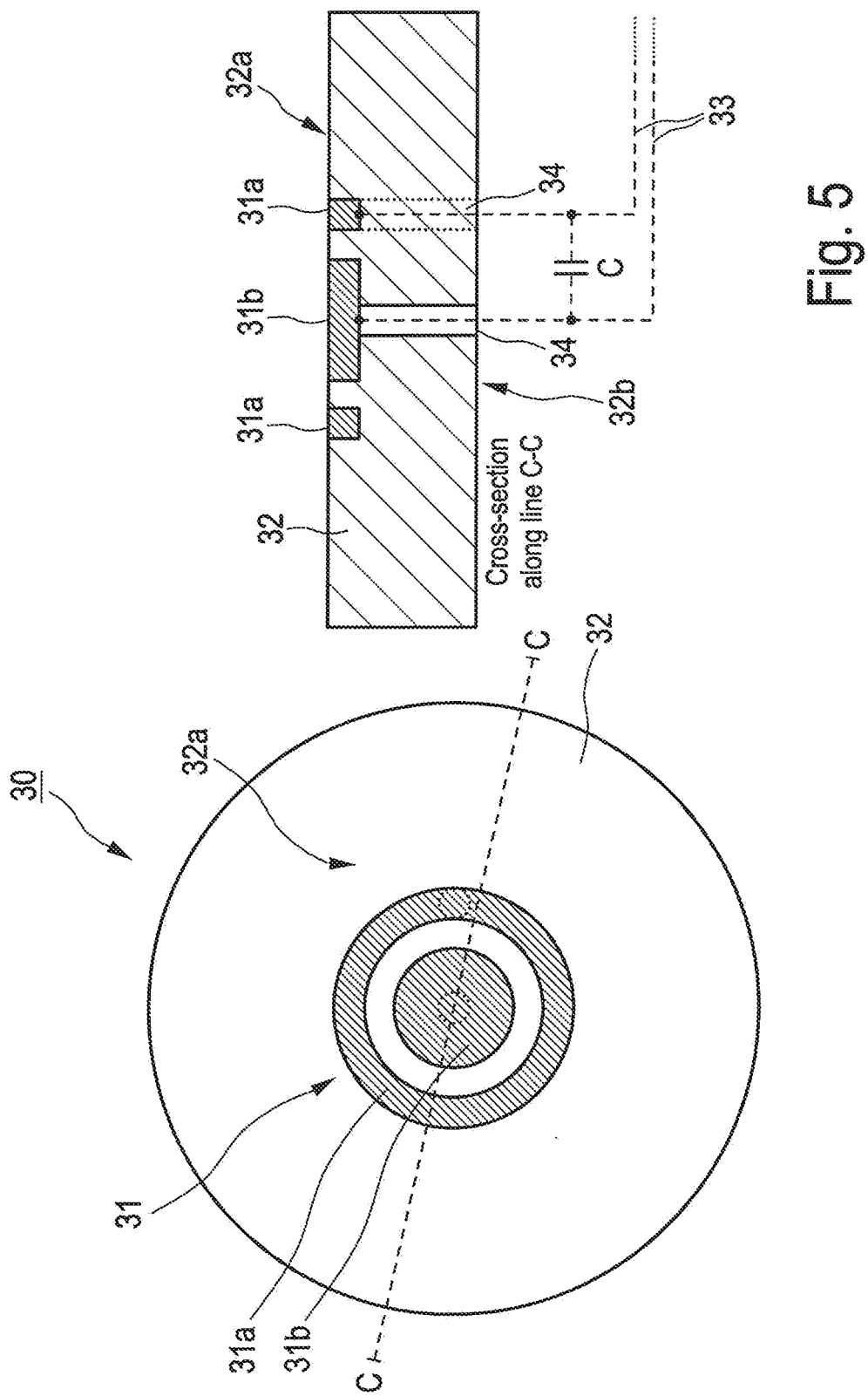
FIG. 5 shows a schematic view of the sensor device in FIG. 1, according to a third embodiment, FIG. 6 (FIGS. 6A, 6B, 6C and 6D) show a schematic view of a sensor device comprising a plurality of individual sensor elements according to a fourth embodiment of the present invention.

The sensor device 30 shown in FIG. 5 is embodied as a capacitive sensor, like the sensor device (10 and 20) according to the first and second embodiments. Sensor device 30 according to the third embodiment includes electrodes 31 comprising an outer electrode 31a and an inner electrode 31b. Inner electrode 31b is preferably designed as a circular area with a predetermined diameter, whereas outer electrode 31a is arranged in the form of an annulus around inner electrode 31b and spaced apart therefrom. Both electrodes 31 are arranged on and fixed to a base plate 32 made of an insulating material and are arranged electrically insulated from each other on a first surface 32a of said base plate 32. The inner and outer electrodes 31a and 31b are each assigned electrically to a particular pole.

According to the present third embodiment in FIG. 5, base plate 32 is formed as a substantially circular disk having a predefined diameter that is larger than the outer diameter of the annular outer electrode 31a. Electrodes 31 may be arranged flush with the first surface 32a of base plate 32 and thus countersunk therein, or electrodes 31 may be arranged wholly or partially outside the material of base plate 32 on the first surface 32a. The first case is shown in the cross-sectional view along line C-C that is shown beside the plan view.

Electrodes 31 arranged on base plate 32 are connected to respective connection lines 33. In the region of each of the two electrodes 31 and their connections to connection lines 33, base plate 32 has respective openings 34 to that end in a second surface 32b opposite first surface 32a, in which connection lines 33 are arranged. Connection lines 33 are guided to the second surface 32b of base plate 32 and outwards from there. The connection lines are guided further to the drive unit 5 shown in FIG. 1, by means of which respective currents and voltages with predefined frequencies are applied to electrodes 31. A capacitor C may be connected between electrodes 31 and thus between the different electrical poles.

Base plate 32 consists of an insulating and solid material, although its disk-shaped embodiment is merely an example. The invention is not limited to such a shape. Rather, any other flat shape may be selected for base plate 32. Whatever the case, a sufficiently planar area (first surface 32a) must be provided for formation of electrodes 31.

The two electrodes 31a and 31b are shown in the plan view on the left in FIG. 5 in an annular or disk-shaped arrangement. However, the invention is not limited to such an arrangement. For example, the inner electrode 31b may also be in the shape of a square, a triangle or a rectangle, in which case the outer electrode 31a otherwise embodied as an annular structure will follow the contour of the inner electrode 31b and be spaced apart therefrom by a predefined distance. The two electrodes 31a and 31b are thus insulated from each other electrically by the insulating base plate 32.

If sensor device 30 according to the third embodiment is arranged in a container like container 2 and preferably in a side wall in the region of the base or in a base wall of container 2, then base plate 32 is sealed against the container wall so that no medium 3 can escape undesirably from the region of the base plate 32 inserted in sensor device 30.

Variants of the First to Third Embodiments

In each of embodiments 1 to 3 as described in the foregoing, a base plate 12, 22 or 32 made of a solid insulating material is provided. Suitable materials for this purpose include various plastics, glass or glass ceramics. The substrate material of base plate 12, 22 and 32 and also of the base plates in the embodiments described below must have a high resistance to water, with as little water as possible being absorbed by the material itself. In order to reduce the penetration of water or other components of medium 3 in container 2, the substrate material, i.e., the surfaces of the base plate are smoothed and polished. The substrate material of base plate 12, 22 and 32 must have electrical properties that are as stable as possible, such as insulation properties and a dielectric constant that is as stable as possible. It is also necessary that the substrate material of base plate 12, 22 and 32 has a predefined strength such that embodying a base plate of the form described above ensures that it can be installed in a mechanically secure manner in an opening of container 2 in the container wall, preferably close to the bottom of the container or in the base of the container itself, and that a seal is assured on a stable, long-term basis. This must be taken into consideration with regard to the operation of a washing device, in particular, in which strong vibrations may occur in conjunction with high spinning speeds of the washing drum.

In the case of the first embodiment, electrodes 11, 21 or 31 shown in the Figures may be made of stainless steel, and the two outer electrodes 11a and the inner electrode 11b may be coated, after appropriate pretreatment, with an electrochemically inert material such as gold. The coating may be applied by sputtering, for example, in which case the electrodes may be coated wholly or at least partially with the inert material (such as gold, for example).

It is necessary that all the surfaces of electrodes 11, 21 or 31, or, in the case of the first embodiment, all of the surfaces coming into contact with medium 3 in container 2, are as smooth as possible in order to prevent even small amounts of water or other substances of medium 3 from penetrating the material of electrodes 11, 21 or 31.

The substrate material of electrodes 11, 21 or 31 in all the embodiments may also be provided in the form of ceramics or glass ceramics, the surface of the parts and components made of these materials (electrodes and/or base plate) being ground and polished to a mirror finish, and a layer containing a inert and electrically conductive material, for example a layer of gold, may be applied after appropriate treatment of the polished surfaces. This layer can be applied by sputtering, for example.

Penetration of water or other ingredients of medium 3 can be prevented by appropriately designing the surfaces of electrodes 11, 21 and 31 (and also of base plate 12, 22 and 32), for example, such that any detrimental effects on measurement results due to changes in the electrical and mechanical properties of electrodes 11, 21 or 31 and of base plate 12, 22 or 32 can be prevented.

In the case of the first embodiment (FIGS. 2 and 3), electrodes 11a and 11b may be made from a ceramic or glass ceramic material, in the respective half-shell design (outer electrodes 11a) or rod-shaped design (inner electrode 11b). After respective preparatory measures, the electrodes are coated with the inert conductive material, for example gold, and subjected to further polishing, if so required. If electrodes 11 of the first embodiment are integral in design, at least one outer electrode may be coated with the inert material on both its outer and inner surfaces (i.e., on the surfaces exposed to the medium). At least the inner surface of the at least one outer electrode 11a lying opposite inner electrode 11b is coated with the inert material and connected galvanically by means of the connection lines. This is also the case in the alternative configuration of the outer electrode in the form of a complete hollow cylinder (provided with openings) in the first embodiment, where at least the inner side (opposite inner electrode 11b) is coated. Connection lines 13 are connected to the respective electrodes 11a and 11b in the coated region, and in the case of multi-part outer electrodes 11e all the parts of outer electrodes 11a are connected to the same terminal (pole).

In the case of the flush electrodes in sensor devices 20 and 30 according to the second and third embodiments, it is possible, after suitable pretreatment of the surface (at least of the respective first surface 22a and 32a) of the respective base plate 22 and 32 to form the pattern and the design of the respective electrodes 21 and 31 using an electrochemically inert material such as gold, for example. The coating may likewise be applied using a sputtering technique. Electrodes 21 and 31 according to the second and third embodiments may also be formed wholly or partially by a metal conductor countersunk in base plate 22 and 23, which may be coated with an inert conductive material (e.g., gold).

In the Figures, respective electrodes 11, 21 and 31 are connected by respective connection lines 13, 23 or 33, the latter being connected for their part to the drive unit 5 shown in FIG. 1. Since electrodes 11, 21 or 31 preferably consist of an electrochemically inert material or are at least coated with such a material (for example, gold), according to the description above, it makes sense not to use any other different metals within each sensor device 10, 20 or 30. The electrodes that are at least coated with gold are preferably contacted, therefore, with gold wire to form the required connection lines 13, 23 and 33. Contact may be effected by bonding or soldering, or it is also possible to use a conductive adhesive.

As a basic principle, the connection lines 13, 23 and 33 of the respective electrodes are not in the region of medium 3, with the result that medium 3 does not flow around them, as that would affect the medium or the connection lines and the points of contact, as well as the electrical properties of the entire sensor arrangement. Instead, connection lines 13, 23 and 33 are arranged in respective indentations or openings in the respective base plate 12, 22 or 32 and are guided to the outside on the side of the respective base plate 12, 22 or 32 (i.e., starting from the second surface 12e. 22a, 32a) which is opposite the side exposed to medium 3 (i.e., on the second surface 12b, 22b, 32b). If so required, connection lines 13, 23 and 33 may be appropriately sealed in this case also by means of temperature-resistant materials, such as plastics, that are also resistant against medium 3.

The respective base plate 12, 22 and 32 thus functions as a carrier plate or as a shared support for the respective multi-part electrode arrangement in the sensor device 10, 20 and 30 described above. In the above description of the embodiments, base plate 12, 22 or 32 is shown as an integral body. However, it may also consist of a plurality of interconnected, sealed parts or of different layers, or may also consist of a plurality of the aforementioned materials, with different parts being made of different materials. In the same manner as in the electrodes of sensor device 1, the materials of the base plate 12, 22 and 32 may be selected from plastics, ceramics or glass ceramics. By appropriately treating the respective surfaces by smoothing and polishing, foreign matter can be prevented from penetrating the material of base plate 12, 22 and 32. This applies in particular to the surfaces exposed to medium 3. The materials may also be connected to one another such that a base plate may comprise a plurality of layers made of different materials, for example.

When the various embodiments of the sensor device according to the above description are put to use, it is also possible to analyze fresh water in water treatment facilities, for example, or domestic or industrial wastewater for contaminant concentrations, or to detect desired or undesired changes in the concentration of substances in the water. This may be useful for water utilities or in cleaning processes with aqueous solutions. Control or regulation procedures can be carried out using the detected values. Cooling media based on aqueous solutions can also be checked for the concentration of additives in the solution.

The respective sensor devices are lines arranged in such a way in container 2, and within a washing device, for example, that medium 3 flows around them, and any undesired deposits on the sensor device are prevented by the respective current. In FIG. 1, arrow P shows the possibility of influencing the washing process in the washing device in container 2, in combination with medium 3, by means of the main control unit 6, which controls or regulates the washing process not only with an internal program using parameters set by the user, but also with detection results from control unit 4.

Fourth Embodiment

A fourth embodiment of the present invention shall now described with reference to FIGS. 6 and 7. Sensor device 40 is arranged, for example, in container 2 according to FIG. 1 and is exposed at least partially to the medium 3 to be analyzed.

Figure 6:
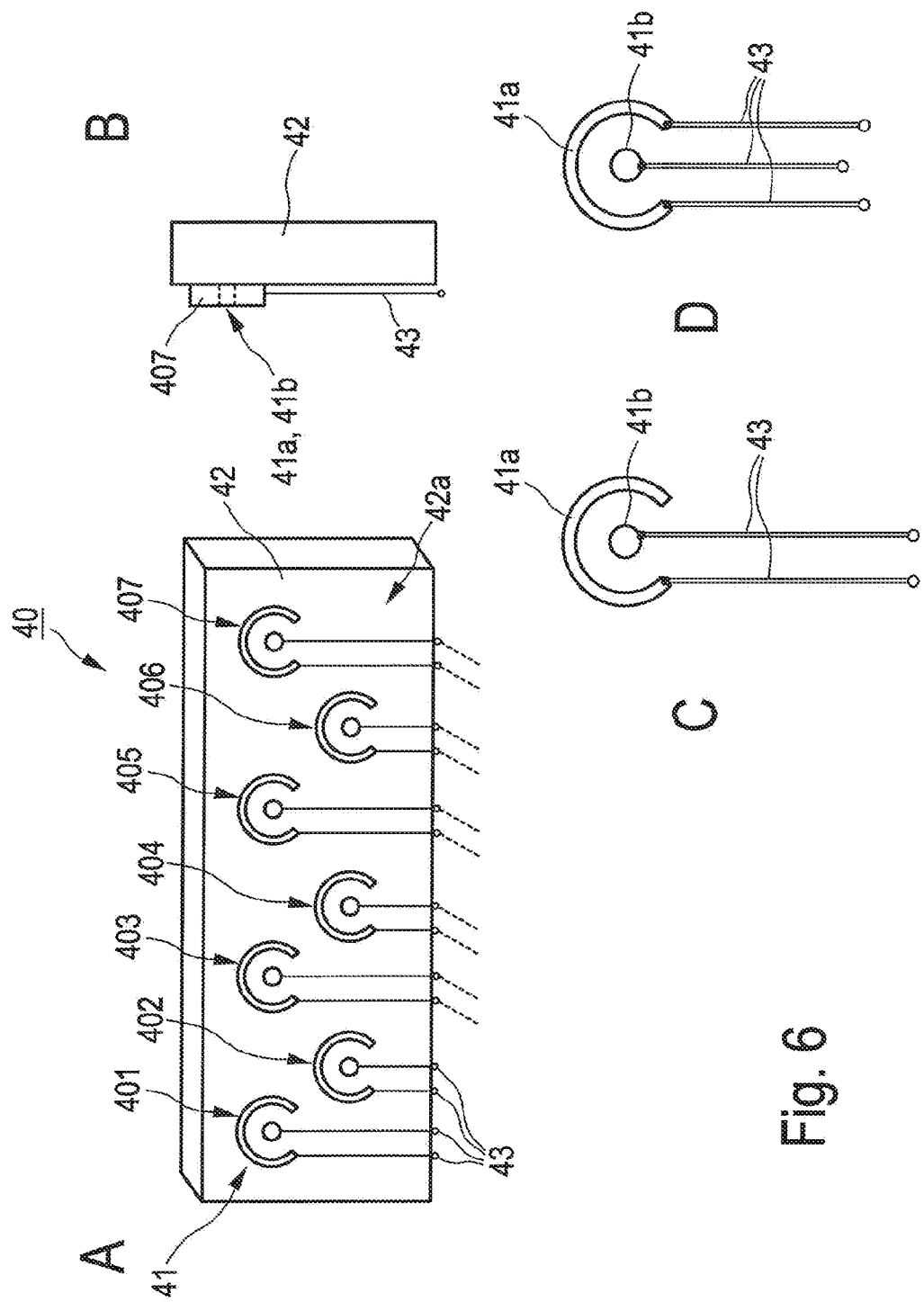

FIG. 6, comprising sub-FIGS. 6A, 6B, 6C and 6D, shows a sensor device 40 according to the fourth embodiment of the present invention, in which electrodes 41 are formed on a base plate 42 in a manner similar to that in the third embodiment. Each set of electrodes 41 comprises an outer electrode 41a and an inner electrode 41b. Each such arrangement of electrodes 41 (41a and 41b) forms a sensor element, with FIG. 6A showing seven such sensor elements 401-407, for example. Sensor elements 401-407 are spatially arranged in a pre-defined manner in relation to each other. Sensor elements 401-407 (a first to seventh sensor element) are distributed on base plate 42, which may be made, for example, of a plastic, of glass, a glass ceramic or a ceramic. The individual electrodes 41a and 41b of the respective sensor elements 401-407 are formed on the suitably prepared surface on one side of base plate 42, wherein electrodes 41 may be arranged in their entirety on said surface or may also be at least partially countersunk into the surface, such that electrodes 41 of sensor elements 401-407 partially project from the respective surface of base plate 42 or are flush with said surface. Base plate 42 is preferably a planar plate of predefined thickness and with a surface which has been prepared to receive the sensor elements.

Each sensor element 401-407 includes connection lines 43, by means of which the individual electrodes 41a and 41b can be connected to a drive unit 5 as shown in FIG. 1, for example. Outer electrode 41a, embodied in the form of a part-ring structure, may be connected by one of connection lines 43, or both ends of outer electrode 41a, which is continuous in a predefined region, may be connected to connection lines 43. The inner (middle) electrode 41b is connected to another one of connection lines 43. By means of drive unit 5 (FIG. 1), different test signals or drive signals (measuring signals, for example voltages and currents as direct quantities or with predefined frequencies) can be applied to the respective electrodes 41 (41a, 41b) in order to perform a measurement.

In the arrangement shown in FIG. 6A, all the sensor elements 401-407 are of substantially the same design, apart from unavoidable tolerances. This means, with regard to performing any measurements, that the individual sensor elements have capacitances that are approximately identical in the relaxed state, i.e., when there is no medium whose properties are to be detected. To perform a measurement, the entire sensor device 40 is brought into contact with the medium 3 whose properties are to be detected, as shown in FIG. 1 (i.e., the medium surrounds or flows around the sensor device), such that one or more measurements can be carried out either with all the sensor elements 401-407, or with a predefined selection of sensor elements, or with individual sensors.

Each individual sensor element 401-407 thus represents an individual sub-capacitance or an individual sensor. Sensor elements 401-407 may be driven collectively (simultaneously) in the same manner, or particular individual sensor elements can be driven by drive unit 5 in a targeted manner and in a respective time sequence, also in different ways, in order to perform a measurement. The individual sensor elements selected to perform a measurement can be connected in series or in parallel, thus resulting in different capacitances and impedances. The option of connecting individual sensor elements in series or in parallel means that, with the different impedances that result, wide frequency ranges or predefined smaller frequency ranges of the drive signals can be processed. It is possible to adjust to different measurement ranges by connecting the sensor elements involved in a particular measurement in series or in parallel, in a predefined manner. It is also possible to make adjustments, in a simple manner, to special properties of a medium 3 being analyzed, or to a particular measuring device (for example drive unit 5 in FIG. 1). By means of drive unit 5 and/or control unit 4, it is possible to define the type of connection between the individual sensor elements, with the measurement likewise being adjusted accordingly. Due to the possibility of setting a predefined impedance (adjustment), electronic circuits for analyzing detected signals can be simpler in design.

More specifically, it is possible for the substantially similar sensor elements 401-407 shown in FIG. 6A to be driven singly by means of drive unit 5, independently of respective other sensor elements, for example with different electrical values such as voltages and frequencies. In this way, different combinations of series and parallel interconnection of the individual sensor elements 401-407 are realized, and it is also possible to connect particular (selected) sensor elements to each other in series, and other sensor elements in parallel.

For example, FIG. 6A shows seven sensor elements 401-407 of sensor device 40, although the invention is not limited to said number of sensor elements. Rather, more or fewer sensor elements may be provided as required.

Regardless of the substantially similar mechanical or geometrical design of sensor elements 401-407 on base plate 42, sensor elements 401-407 and their associated electrodes 41 (41a, 41b) may be made of a similar conductive material that is applied to base plate 42. Individual ones of sensor elements 401-407, or groups of sensor elements (a selection from sensor elements 401-407) may consist of different materials. Possible materials for embodying respective sensor elements 401-407 and hence the respective electrodes 41 are gold, platinum and chromium, for example. In connection with a measurement, individual sensor elements 401-407 made of different materials can also be driven differently by means of drive unit 5 in FIG. 1. Analysis of the output signals from the respective sensor elements 401-407 in connections with a measurement can also be made dependent on the particular material that the respective sensor element 401-407 is made of.

Figure 7:
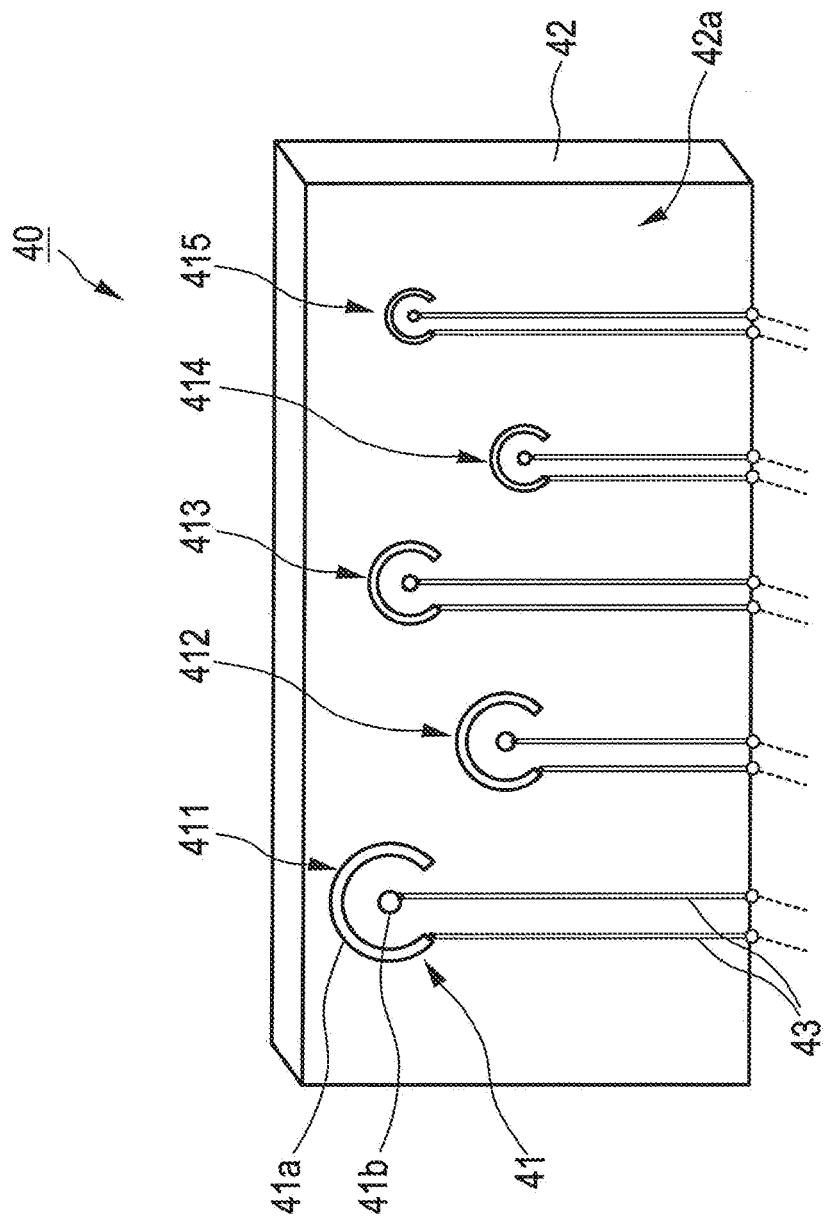
FIG. 7 shows a schematic view of a variant of the sensor device in FIG. 6, with a plurality of different sensor elements, FIG. 8 (FIGS. 8A and 8B) shows a schematic view of a sensor device according to a fifth embodiment, with a sensor plates arranged opposite one other.

FIG. 7 shows a similar arrangement of individual sensor elements, for example of sensor elements 411-415 as shown in FIG. 6A. A plurality of sensor elements 411-415 is likewise provided, although the sensor elements of sensor device 40 each have a different size (i.e., different dimensions), in contrast to the arrangement in FIG. 6A. The respective arrangement of the sensor elements, and in particular of electrodes 41 (outer electrode 41a and inner electrode 41b), entails different mechanical (geometrical) dimensions of the various sensor elements 411-415. The arrangement according to FIG. 7 thus includes sensor device 40 with the five sensor elements 411-415. For example, and all of the sensor elements 411-415 with different dimensions may be made of the same material or of different materials. In the same way as in the arrangement according to FIG. 6A, individual sensor elements or all the sensor elements 411-415 or groups thereof can be driven by means of drive unit 5 in FIG. 1 when a measurement is to be performed. The individual sensor elements 411-415 may be arranged on the preferably planar base plate 42 in a manner similar to that shown in FIG. 6A. Each sensor element 411-415 has the connection lines 43 that are required in order to be driven.

Possible materials for the individual electrodes of sensor elements 411-415 are likewise gold, platinum, chromium and the like (i.e., metal coatings). To form the respective electrodes, the coatings can be applied by sputtering, for example, onto the suitably prepared surface of the base plate.

FIG. 6 shows seven sensor elements 401-407 on base plate 42, for example, and in FIG. 7, for example, there are five sensor elements 411-415 arranged on base plate 42. The present invention shall now be described with reference to said Figures. However, it is not confined to the number or arrangement of the respective sensor elements 401-415. Rather, a larger or a smaller number of sensor elements may be provided in any arrangement on the respective base plate 42. In any case, each of the sensor elements is accessible from the outside via individual connection lines 43 and can thus be driven externally, which means that each sensor element 401-415 can be driven separately or as part of a group.

In the same manner as shown in FIG. 6A, the individual sensor elements 411-415 in FIG. 7 represent individual capacitances of different kinds, and different materials can also be taken into consideration. The arrangement according to FIG. 7, with the five sensor elements 411-415, is thus a 5-sub-capacitances sensor array. The respective sensor elements 411-415 are exposed to medium 3 to be analyzed, and measurement can be performed by providing electrical signals (voltages, currents, frequencies). Predefined connections in series or in parallel, to set a particular impedance or capacitance, are possible in the same way as described in connection with the sensor arrangement according to FIG. 6. Other ways of setting different capacitances and impedances by driving the individual sensor elements separately ensue from the different sizes of the sensor elements in FIG. 7 and from their different electrical properties.

In addition to capacitive measurements, it is also possible with the sensor device, in identical or similar configuration, to apply inductive and resistive measurement techniques, or a combination thereof. With the sensor device arrangement according to FIGS. 6A and 7, comprising a plurality of individual sensor elements of the same or different kind, a multisensor array is formed in which it is possible, by driving all the sensor elements 401-415, or individual ones or a group of sensor elements 401-415, to adjust the sensitivity of sensor device 40 selectively to a measurement procedure, a measurement set-up and/or a medium 3 to be analyzed. It is possible in this regard to adjust the impedance of the respective sensor device 40 to given conditions or to an analyzer, by arranging a plurality of individual sensor elements 401-415 accordingly, such that all or individual sensor elements of different sizes and made of different materials can be driven selectively.

In the arrangement according to FIG. 7, comprising sensor elements 411-415 of different sizes, the sensors may differ in size by particular ratios. For example, the area of the individual sensor elements may be dimensioned in such a way that the second largest area is equal to half that of the largest area, the third largest area is equal to half that of the second largest, the fourth largest area equal to half that of the third largest, etc. In this way, the effective areas of the individual sensor elements 411-415 are each in a predefined ratio to each other, so it is possible by connecting the individual sensor elements appropriately in series or in parallel (thus forming sub-sensors) to set the total capacitance of sensor device 40 in gradations. The number of sensor elements or sub-sensors is equal to the number of bits. For example, if eight sensor elements (sub-sensors) are provided, this equates to an 8-bit system, and if driven appropriately by drive unit 5 the capacitance can be set in 256 gradations.

In deviation therefrom, it is also possible to form other ratios between the sizes of the individual sensor elements on base plate 42. Different sensitivities of the sensor device (capacitances and impedances) can also be set in this regard.

Base plate 42 is a carrier and consists of an insulating material, for example a plastic, a ceramic, a glass ceramic or glass. The individual electrodes 41 of sensor elements 401-415 can be applied by sputtering. However, other methods, such as gluing or galvanization, are also possible as ways of applying the respective materials to the surface of base plate 42.

In the fourth embodiment according to FIGS. 6A and 7, base plate 42 is a planar area having a predefined thickness, depending on the material being used and the area (number of sensor elements) required. However, the invention is not limited to the latter. Rather, the base plate may also have a curved or spherical surface on one or both sides, on which the respective sensor elements 401-415 can be arranged. The sensor elements 401-415 described in the foregoing may be formed on just one of the surfaces of base plate 42 or on both surfaces (i.e., on both sides). Sensor device 40 is arranged, for example, in container 2 according to FIG. 1, and the medium 3 to be analyzed flows at least partially around said device.

Fifth Embodiment

A sensor device according to a fifth embodiment of the present invention shall now be described with reference to FIG. 8. Sensor device 50 is arranged, for example, in container 2 according to FIG. 1 and is exposed at least partially to the medium 3 to be analyzed.

Figure 8:
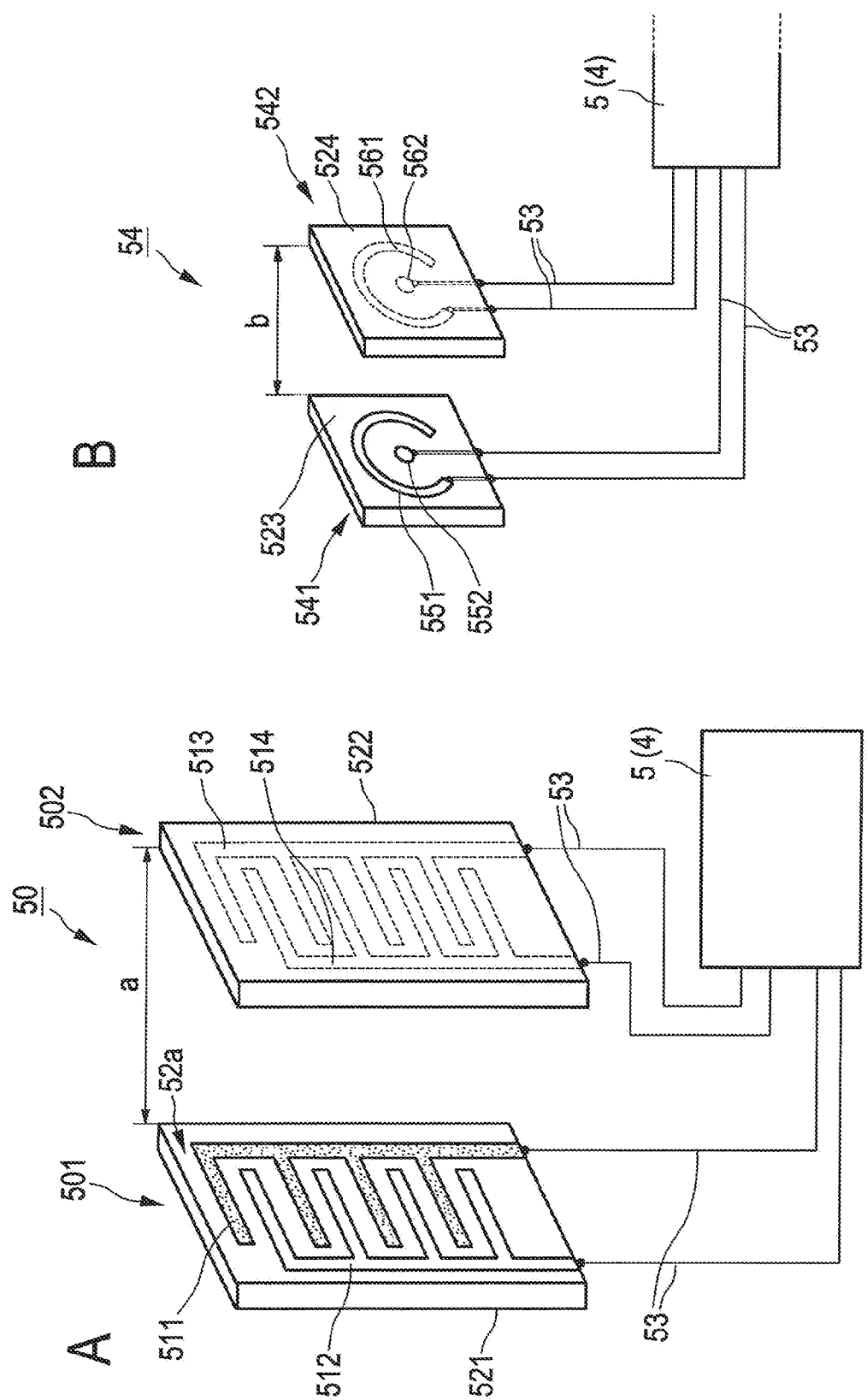

FIG. 8 and FIG. 8A, in particular, show an arrangement of a sensor device 50, in which two individual sensor elements 501 and 502 (first and second sensor elements) are arranged substantially parallel to and opposite each other. The first and the second sensor elements 501 and 502 each consist of a substantially planar base plate 521 and 522, which lie opposite each other to form a parallel-plate capacitor, a first pair of electrodes 511 and 512 being arranged on the first base plate 521 of the first sensor element 501 and a second pair of electrodes 513 and 514 being arranged on the second base plate 522 of the second sensor element 502. The respective electrode pairs 511 and 512, 513 and 514 consist of an inter-digitated arrangement of intermeshing electrode pairs, as similarly described in connection with the second embodiment. The respective electrode pairs 511, 512 and 513, 514 are located on the inner, opposite surfaces of the respective base plates 521 and 522, and are of mirror-symmetrical construction, such that the same parts of one pair of electrodes (e.g., 511) are opposite the respective other parts of the other pair of electrodes (e.g., 513).

The electrode pairs are each connected via connection lines 53 to drive unit 5 according to FIG. 1, or also to control unit 4, if the function 1 of drive unit 5 and also a respective function of analyzing the sensor output signals are performed in the sensor control unit 4 according to FIG. 1.

Possible materials for the electrodes of the respective electrode pairs 511 and 512 are the materials specified in the foregoing, such as gold, platinum, chromium or rhodium. The respective conductive materials of electrode pairs 511 and 512, 513 and 514 can be applied by sputtering or by some other appropriate technique. Materials may be provided, more specifically, that are sensitive to particular ions.

According to FIG. 8A, the two opposite sensor elements 501 and 502 of sensor device 50 are embodied substantially similarly. To perform a measurement, individual electrodes of the respective sensor elements 501 and 502, or all of the electrodes of electrode pairs 511 and 512, 513 and 514 can be driven and analyzed for their detection results. Preferably, respective opposite electrodes are driven together.

FIG. 8B shows an arrangement alternative to the one in FIG. 8A, showing the arrangement of a sensor device 54 in which the electrode arrangements as shown in connection with the fourth embodiment are used, instead of the interdigitated arrangement (interdigitated structure) shown in FIG. 8A. The electrode arrangements consist of an inner electrode and an outer electrode in the form of a part-ring disposed around said inner electrode.

More specifically, a first sensor element 541 comprises an outer electrode 551 and an inner electrode 552, which are formed on a base plate 523. On another base plate 524 that is likewise substantially planar, the same structure of electrode arrangement (electrodes 561 and 562) is formed mirror-symmetrically, one opposite the other, so that the two sensor elements 541 and 542, similarly to those in FIG. 8A, are arranged in approximately the same way, one opposite the other, to form a parallel-plate capacitor. Lines 53 are provided to establish a connection to a drive unit 5 or a control unit 4 (FIG. 1).

Sensor elements 501, 502, 541 and 542 are spatially arranged in a predefined manner in relation to each other, the respective base plates being spaced apart at a distance a (FIG. 8A) or b (FIG. 8B) from each other. By driving individual sensor elements, it is possible to set different sensitivities for the sensor device as a whole. The respective sensor elements 501, 502, 541 and 542 are exposed at least partially to medium 3 being analyzed (FIG. 1), such that the electrical properties of the respective sensor elements are affected by medium 3, and measurement can be performed regarding the properties of medium 3 being analyzed. The respective base plates 511-514 may be made, for example, of a plastic, of glass, of a glass ceramic or a ceramic.

The materials used for the arrangement in FIG. 8B are the same as those used for sensor elements 501 and 502 in FIG. 8A and for the sensor elements (401-415) that were described in connection with the fourth embodiment.

Figure 9:
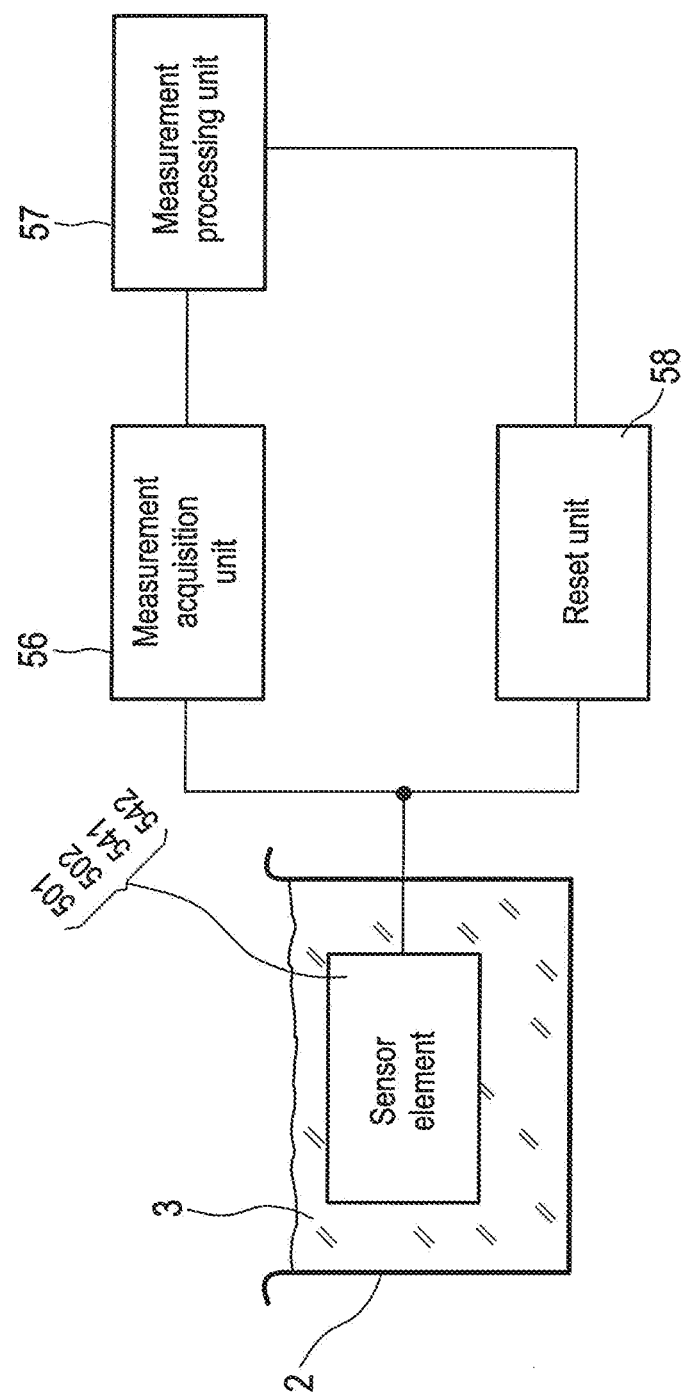
FIG. 9 shows a schematic view of a sensor element according to FIG. 8 being selected for detection of measured values and for performing a reset.

FIG. 9 shows a simplified and schematic block diagram for illustrating how sensor elements 501, 502, 541 and 542 are driven according to the fifth embodiment. The respective sensor elements 501 and 502 or 541 and 542 are arranged in container 2 (FIG. 1), where they are surrounded by medium 3. The respective sensor elements are electrically connected to a measurement acquisition unit 56, which functions similarly to drive unit 5. Electrical signals with respective currents, voltages and frequencies are supplied to drive the respective sensor elements 501, 502, 541 and 542. Measured values are likewise detected, and the detected electrical signals are fed to a measurement processing unit 57, where the detected electrical signals from the respective sensor elements 501, 502, 541 and 542 are processed, at least partially in connection with previously stored base values acquired experimentally.

According to FIG. 9, a reset unit 58 is also provided, by means of which sensor elements 501, 502, 541 and 542 are driven so that medium 3 between and surrounding the respective plates of the sensor elements can be restored to a predefined state electrically and in respect of the properties of medium 3. This predefined state can be achieved, for example, by applying particular electrical variables to the electrodes of the respective sensor elements 501, 502, 541 and 542, thus achieving a definitive state of the medium and the surroundings of the respective sensor elements 501, 502, 541 and 542. Proceeding from this defined state of the sensor surroundings, a further measurement (or several measurements) can be performed in combination with impedance spectroscopy and the supplying of electrical signals, in particular electrical signals having predefined frequencies.

If, in accordance with the fifth embodiment, sensor elements 501, 502, 541 and 542 in FIG. 9 are brought into a predefined state by means of the reset unit, in connection with medium 3 surrounding sensor elements 501, 502, 541 and 542 (with regard to predefined properties, or properties of special interest), such preparation allows more precise and useful measurements to be obtained on the basis of predefined ambient conditions around sensor elements 501, 502, 541 and 542.

Sixth Embodiment

A sixth embodiment of the present invention shall now described with reference to FIGS. 10, 11 and 12.

Figure 10:
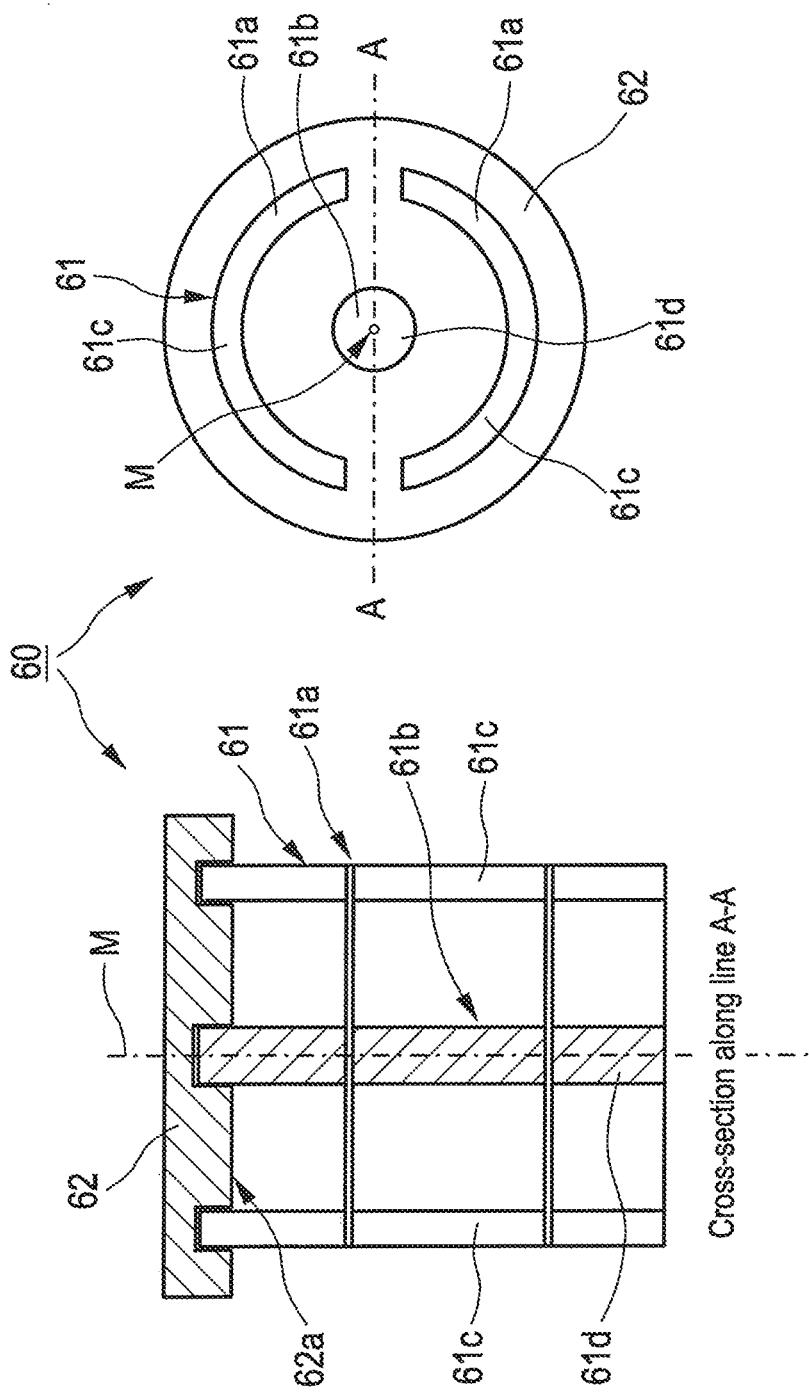
FIG. 10 shows a schematic view of a sensor device according to a sixth embodiment.

FIG. 10 shows the arrangement of a sensor device 60, mainly showing a cylindrical capacitor similar to the one already described in connection with the first embodiment. Sensor device 60 is arranged, for example, in container 2 according to FIG. 1 and is exposed at least partially to the medium 3 to be analyzed.

Electrodes 61 comprising at least one outer electrode 61a (or outer electrode) and an inner electrode 61b (or inner or middle electrode) are arranged on a base plate 62 made of an insulating material. In the present embodiment, two outer electrodes 61a are provided that are arranged concentrically and with gaps around inner electrode 61b, such that a cylindrical capacitor is formed and such that medium 3 to be analyzed can flow at least partially around electrodes 61a and 61b inside and outside outer electrode 61a. Base plate 62 may be made, for example, of a plastic, of glass, of a glass ceramic or a ceramic.

Unlike the electrode arrangement of sensor device 10 (to form a cylindrical capacitor) according to the first embodiment (FIGS. 2 and 3), the respective electrodes 61a and 61b according to the sixth embodiment are provided in a plurality of parts in a direction of extension along a line M. The at least one outer electrode 61a (or both outer electrodes 61a concentrically arranged about the inner electrode (middle electrode) 61b) is subdivided along along line M in the same way as the middle electrode 61b. The preferably planar base plate 62 made of an insulating material is used here as an insulating holding device for sensor device 60 and especially for electrodes 61a and 61b.

The multi-part embodiment of the respective electrodes 61a and 61b in the direction of extension along line M, according to the sixth embodiment described above, can be obtained a first way by embodying the at least one outer electrode 61a on a cylinder segment 61c (having a square and preferably rectangular two-dimensional net) made of one piece of non-conductive material. The selection of materials for the respective base plate of the previous embodiment can be used for selecting the material for cylinder segment 61c. Individual parts of the outer electrode 61a can be formed flush and insulated from each other on integral cylinder segment 61c. The integral embodiment of cylinder segment 61c of the at least one outer electrode is shown by way of example in FIG. 11A, described below.

According to FIGS. 10 and 12, the multi-part embodiment of the respective electrodes 61a and 61b in the direction of extension along line M, according to the sixth embodiment, can be obtained a second way, for example by forming the at least one outer electrode 61a on a multi-part cylinder segment 61c. The individual parts of the multi-part cylinder segment 61c correspond to the respective parts or active areas of electrode 61a in the arrangement along line M. The respective active areas are referred to in the following as electrode sections.

The integral or multi-part embodiment, described above, of the at least one outer electrode 61a formed in connection with a cylinder segment 61c is also applied in a similar way to the inner electrode (middle electrode) 61b. According to FIG. 10, inner electrode 61b can be embodied in the form of an integral rod or hollow cylinder 61d made of an insulating material (like base plate 62). Alternatively, the rod or hollow cylinder 61d may also have a multi-part construction, as shown in FIGS. 10-12. The respective active areas of inner electrode 61b (referred to in the following as electrode sections) are applied to the integral or multi-part rod or hollow cylinder 61d and insulated from each other.

Figure 11:
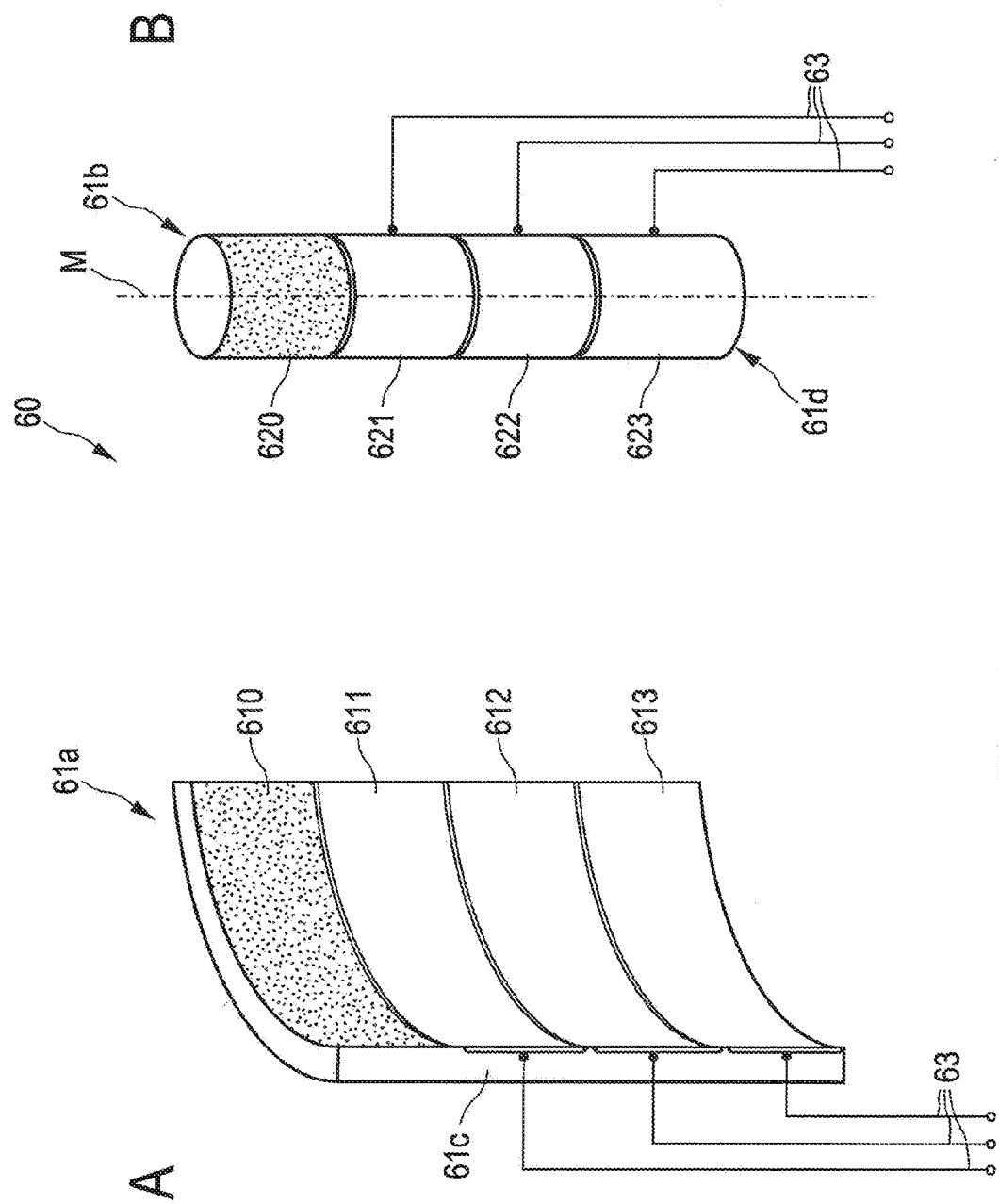
FIG. 11 shows a schematic view of parts of the sensor element according to FIG. 10, in first variant.

Further details concerning the distribution of the electrodes 61 of sensor device 60 are shown in FIGS. 11 and 12.

FIG. 11A shows details of outer electrode 61a, and FIG. 11B shows details of inner electrode 61b. As shown with regard to the first embodiment according to FIG. 2, connection lines 63 are provided for driving the respective electrodes 61.

This is indicated in FIGS. 11 and 12 and omitted in FIG. 10 to simplify the view being shown.

FIG. 11A shows the at least one outer electrode 61a. In this Figure, starting from the top, a first part of outer electrode 61a is provided as a fixing section 610 which is used to fix outer electrode 61a in base plate 62.

In the direction of extension of outer electrode 61a along line M, a first electrode section 611, a second electrode section 612 and a third electrode section 613 are provided, for example. Electrode sections 611-613 each form a part of outer electrode 61a and can be singly (separately, individually) driven by means of respective connection lines 63. The respective electrode sections 611-613 are formed and insulated from each other on a shared electrode member in the form of cylinder segment 61c of outer electrode 61a.

Inner electrode 61b in FIG. 11B is similarly structured. Viewed from the top down, as shown in FIG. 11B, inner electrode 61b comprises a fixing section 620 and successive electrode sections 621, 622 and 623, each of which are connected to connection lines 63.

Outer electrode 61a and inner electrode 61b are thus structured in approximately the same manner, with the respective electrode sections 611-613 and 621-623 in the direction of extension along line M being of equal size. Electrode sections 621-623 are likewise insulated from each other.

Due to the arrangement of the outer and inner electrodes 61a and 61b of sensor device 60, with the structure shown in FIGS. 11A and 11B, the respective individual capacitances are formed inside the sensor device 60 that is substantially embodied as a cylindrical capacitor, wherein corresponding electrode sections 611-613 of outer electrode 61a are opposite the electrode sections 621-623 of inner electrode 61b. It is possible for all the electrode sections or for individual electrode sections 611-613 and 621-623 to be used to perform a measurement, due to the electrodes being driven by means of the respective connection lines 63. It is possible in this regard for the capacitances and hence the impedances to be adjusted to predefined conditions.

FIG. 12 shows an alternative embodiment of the sixth embodiment in connection with sensor device 60. Outer electrode 61a and inner electrode 61b are subdivided in a similar manner into various sections. A first section of outer electrode 61a is used as a fixing section 640 for fixing the outer electrode in base plate 62 (FIG. 10). The outer electrode 61b also includes first to fourth electrode sections 641, 642, 643 and 644, which extend along line M. Electrode sections 641-644 are formed in the same manner on a shared (integral or multi-part) support for outer electrode 61a in the form of cylinder segment 61c and are insulated from each other so that they they can be driven individually (separately) or collectively via connection lines 63.

Inner electrode 61b according to FIG. 12B has a structure corresponding to that of outer electrode 61a, a fixing section 650 being used to fix said inner electrode in base plate 62. Further electrode sections 651, 652, 653 and 654 extend on inner electrode 61b along line M. The respective electrode sections 651-654 are insulated from each other and can be externally driven, either individually or collectively, via respective connection lines 63 connected thereto.

In comparison with the arrangement of the respective electrode sections 611-613 and 621-623 according to FIGS. 11A and 11B, the electrode sections 641-644 and 651-854 as shown in FIGS. 12A and 12B have a different extension along line M. In FIGS. 12A and 12B, the respective first electrode section 641 and 651, for example, has the smallest extension, whereas the fourth electrode section 644 and 654 has the largest extension in the direction of line M. The longitudinal extensions of the respective electrode sections of outer electrode 61a and inner electrode 61b correspond to each other in each case, which means that, by driving respective corresponding electrode sections via the individual connection lines 63, it is possible to monitor sub-capacitances (impedances) of a cylindrical capacitor, which have different capacitance values, and therefore different impedances as well, depending on the size of the respective corresponding electrode sections 641-644 and 651-654.

More specifically, in the case of outer electrode 61a according to FIGS. 11A and 12A, the single electrode section 611-613 and 641-644 is part of an inner cylinder to which a particular area (active area) can be assigned. An annular area (active area) can be similarly assigned to the annular electrode sections 621-623 and 651-654 of the respective inner electrode 61b in FIGS. 11B and 12B. In FIG. 12B, areas A1, A2, A3 and A4 are specified for the respective annular areas of electrode sections 651-654. Regardless of the simplified and schematic view according to FIG. 12B, the respective annular areas A1-A4 stand in a predefined relationship to each other. For example, annular area A4 of the fourth electrode section 654 may be double the annular area A3 of the third electrode section 653. The annular area A3 of the third electrode section 653 may also be double the annular area A2 of the second electrode sections 652. In the same manner, the annular area A2 of the second electrode section 652 may be double the annular area A1, for example, of the first electrode section 651.

In accordance with the ratios $A4=2\times A3=4\times A2=8\times A1$, relative ratios may therefore ensue between the annular areas A1-A4, taking the example of inner electrode 61b. This also applies in a similar way to the area ratios of outer electrode 61a (sub-areas of electrode sections 641 and 644). However, the invention is not limited to this example of integer ratios. Rather, other ratios between the areas of the electrode sections (ratios between active areas) may also be specified.

It is possible in this way to form sub-capacitances by means of sensor device 60 in the form of a cylindrical capacitor, depending on the respective size of annular areas A1-A4 or of the active areas, wherein the sub-capacitances and thus the impedances as well may have predefined ratios between each other.

In FIGS. 11A, 11B, 12A and 12B, the respective connection lines 63 are shown schematically and are connected to the respective electrode sections 611-613, 621-623, 641-644 and 651-654. Connection lines 63 may be guided in the outer region of the respective inner or outer electrode 61a and 61b, or may be guided inside the substrate material (cylinder segment 61c and rod or hollow cylinder 61d) of the respective electrode, so that the outer surface, and hence the active surface, of the respective electrode sections is not adversely affected by the path of connection lines 63.

Respective sub-sensors (sub-capacitances, sub-impedances) are formed by the different electrode sections 611-613, 621-623, 641-644 and 651-654, and said sub-sensors can be driven separately, according to the above specifications, so that they can be used singly or collectively to perform a measurement. It is possible in this way to adapt the sensors to the anticipated properties of a mediums 3 being measured, or to a measurement system or analyzer. It is possible, therefore, to set the respective sensor device to different sensitivities in connection with the medium 3 being analyzed and an analysis obtained with the arrangements described above.

The respective electrode sections 611-613, 621-623, 641-644 and 651-654, specified above, of sensor device 60 according to both variants of the sixth embodiment may be made of the same material, such as gold, platinum, chromium or rhodium (and the like), and the coating may be applied by sputtering or by some other suitable technique. It is also possible for respective electrode sections to be made of a different material from that of other electrode sections, and any combination of materials is possible. For example, the first electrode section 651 may be made of gold, the second electrode section 652 of platinum, the third electrode section 653 of rhodium and the fourth electrode section 654 of chromium, with the respective metals being applied to the substrate material of inner electrode 61 (FIG. 12B).

It is possible in this way to influence or change the capacitive properties and other properties of the respective subsensors (sub-capacitances) and thus to influence or change the entire sensor device 60 according to the materials used, and specific materials can be adapted for specific ions. It is also possible for the various electrode sections to have the same or different surface characteristics (such as different roughness, for example). Sensor device 60 as a whole can be set to different sensitivities.

In any case, the active areas of electrode sections 611-613, 621-623, 641-644 and 651-654 of sensor device 60, as specified above, can be exposed wholly or at least partially to the medium 3 being analyzed. It is preferred that the medium 3 being analyzed flows through the arrangement of the cylindrical capacitor according to FIG. 10. The surfaces of the respective active areas of individual electrode sections may also be provided with special protective layers.

As in the view shown in connection with the fourth embodiment, it is therefore possible to form sub-sensors according to a multi-bit system, wherein the capacitance or the impedance can be set in a predefined number of gradations and can be adjusted to suit predefined conditions.

In FIGS. 11A and 11B, the device according to the sixth embodiment is described in connection with three respective electrode sections of outer and inner electrodes 61a and 61b. According to FIGS. 12A and 12B, four electrode sections are provided in each case. However, the present invention is not limited to a fixed number of electrode sections or to the ratios between areas as specified in the foregoing. Rather, more or fewer electrode sections may be provided in a respectively similar manner for outer and inner electrodes 61a and 61b.

In the description of the above embodiments, the respective electrodes of the individual sensor elements are connected to connection lines, for example to connection lines 43 according to the fourth embodiment. The respective connection lines are combinations of electrically insulated lines, said insulation applying to the course of the connection lines outside the base plate (here, for example, base plate 42 in FIGS. 6 and 7) and also to the course of base plate 42. Insulated lines are provided outside the base plate, whereas on base plate 42 connection lines 43 are guided to the electrodes and are connected thereto. The electrical insulation is provided by the connection lines being covered with an insulating layer throughout their path on base plate 42 and are free of such insulation only in the region of the electrodes. These measures described in connection with the fourth embodiment can be applied to all the connection lines in the embodiments described in the foregoing. Uninsulated connection lines can lead to distorted measurement results, depending on the type of measurement being conducted and the drive signals being used.

The present invention has been described in the foregoing with reference to embodiments of the sensor device. However, for a skilled person engaged in this field, it is self-evident that the configuration of the present invention according to the Figures described above, and the reference signs used for the respective parts and components in the Figures and the description, and the details provided by way of example are not to be interpreted in a limiting sense. The invention is not limited to the views shown in the Figures, or, more specifically, to dimensions, arrangements or forms of the components. All embodiments and variants which come under the enclosed claims are considered to belong to the invention.

The invention claimed is:

1. A sensor device for detecting properties of fluid media in a container, comprising
   a base plate made of an insulating material and having at least one first surface exposed to the medium,
   at least one sensor element embodied as a cylindrical capacitor and comprising at least one outer electrode and one inner electrode partially surrounded by said outer electrode, wherein the at least one outer and the inner electrode extend from the first surface of the base plate, and
   wherein the at least one outer electrode and the inner electrode are subdivided in the direction of extension into a plurality of electrode sections insulated from each other and the outer and the inner electrode are subdivided in the same manner.

2. The sensor device of claim 1, wherein the electrode sections of the outer and inner electrodes are each connected to connection lines and can be driven individually and independently of each other.

3. The sensor device of claim 1, wherein the individual sensor elements are made of the same conductive material or of different conductive materials.

4. The sensor device of claim 1, wherein the separate electrode sections are made of the same conductive material or of different conductive materials, and wherein respectively matching electrode sections of the outer and inner electrodes are made of the same material.

5. A sensor device for detecting properties of fluid media in a container, comprising
   a base plate made of an insulating material and having at least one first surface exposed to the medium,
   at least one sensor element embodied as a cylindrical capacitor and comprising at least one outer electrode and one inner electrode partially surrounded by said outer electrode, wherein the at least one outer and the inner electrode extend from the first surface of the base plate,
   wherein the at least one outer electrode and the inner electrode are subdivided in the direction of extension into a plurality of electrode sections insulated from each other and the outer and the inner electrode are subdivided in the same manner, and
   wherein the at least one outer and the inner electrode are subdivided into a plurality of identical or different electrode sections and the electrode sections formed by non-identical subdivision are subdivided in respect of their extension in the direction of extension in predetermined ratios in relation to each other.

6. The sensor device of claim 5, wherein the separate electrode sections are made of the same conductive material or of different conductive materials, and wherein respectively matching electrode sections of the outer and inner electrodes are made of the same material.

7. A sensor device for detecting properties of fluid media in a container, comprising
   a base plate made of an insulating material and having at least one first surface exposed to the medium, and at least one sensor element embodied as a cylindrical capacitor and comprising at least one outer electrode and one inner electrode partially surrounded by said outer electrode, wherein the at least one outer and the inner electrode extend from the first surface of the base plate, wherein the at least one outer electrode and the inner electrode are subdivided in the direction of extension into a plurality of electrode sections insulated from each other and the outer and the inner electrode are subdivided in the same manner;

wherein the electrode sections of the outer and inner electrodes are each connected to connection lines and can be driven individually and independently of each other; and wherein the at least one outer and the inner electrode are subdivided into a plurality of identical or different electrode sections and the electrode sections formed by non-identical subdivision are subdivided in respect of their extension in the direction of extension in predetermined ratios in relation to each other.

8. The sensor device of claim 7, wherein the separate electrode sections are made of the same conductive material or of different conductive materials, and wherein respectively matching electrode sections of the outer and inner electrodes are made of the same material.

\* \* \* \* \*